US006967093B2

(12) United States Patent
Bistrup et al.

(10) Patent No.: US 6,967,093 B2
(45) Date of Patent: *Nov. 22, 2005

(54) GLYCOSYL SULFOTRANSFERASE-3

(75) Inventors: Annette Bistrup, San Francisco, CA (US); Steven D. Rosen, San Francisco, CA (US); Stefan Hemmerich, Berkeley, CA (US)

(73) Assignees: The Regents of the University of California, Oakland, CA (US); Syntex (U.S.A) LLC, Palo Alto, CA (US)

( * ) Notice: Subject to any disclaimer, the term of this patent is extended or adjusted under 35 U.S.C. 154(b) by 339 days.

This patent is subject to a terminal disclaimer.

(21) Appl. No.: 09/816,825

(22) Filed: Mar. 22, 2001

(65) Prior Publication Data

US 2001/0051370 A1 Dec. 13, 2001

Related U.S. Application Data

(63) Continuation of application No. 09/045,284, filed on Mar. 20, 1998, now Pat. No. 6,265,192.

(51) Int. Cl.[7] .......................... C12P 21/06; C12N 9/00; C12N 9/10; C07H 21/04
(52) U.S. Cl. .............................. 435/193; 435/4; 435/6; 435/69.1; 435/183; 435/192; 435/252.3; 435/320.1; 435/325; 536/23.2; 536/23.5
(58) Field of Search ............................ 435/4, 6, 69.1, 435/183, 193, 194, 252.3, 320.1, 200, 325; 536/23.2–23.7, 24.1–24.33; 514/44

(56) References Cited

U.S. PATENT DOCUMENTS

| | | | |
|---|---|---|---|
| 5,185,326 A | 2/1993 | Muller et al. | |
| 5,227,369 A | 7/1993 | Rosen et al. | |
| 5,318,890 A | 6/1994 | Rosen et al. | |
| 5,340,934 A | 8/1994 | Termine et al. | |
| 5,580,862 A | 12/1996 | Rosen et al. | |
| 5,695,752 A | 12/1997 | Rosen et al. | |
| 6,265,192 B1 * | 7/2001 | Bistrup et al. | 435/193 |
| 2002/0164748 A1 * | 11/2002 | Bistrup et al. | 435/193 |

FOREIGN PATENT DOCUMENTS

| | | |
|---|---|---|
| EP | 0 821 066 A1 | 1/1998 |
| EP | 1130094 | 9/2001 |
| WO | WO 92/13102 | 8/1992 |
| WO | WO 00/14251 | 3/2000 |
| WO | WO 00/58473 | 10/2000 |
| WO | WO 01/85177 | 11/2001 |

OTHER PUBLICATIONS

Aparicio et al. (PIR Database, Accession NoT30228,) Gene, vol. 169:9–16, 1996.*
Lifeseq clone#2617407 Bistrup et al., Mar. 22, 2001.
Lifeseq clone #2620445 Bistrup et al., Mar. 22, 2001.
Bistrup et al., 1999, *J. Cell Biol.* vol. 145: 899–910.
Baumhueter, Susanne, et al., (1993) "Binding of L–Selectin to the Vascular Sialomucin CD34," *Science*, vol. 262:436–438.
Bertozzi, Carolyn, et al., (1995) "Sulfated Dissacharide Inhibitors of L–Selectin: Deriving Structural Leads from a Physiological Selectin Ligand," *Biochemistry*, vol. 34(44):14271–14278.
Boukerche, Habib, et al., (1996) "A Monoclonal Antibody Directed Against A Granule Membrane Glycoprotein (GMP–140/PADGEM, P–Selcetin, CD62P) Inhibits Ristocetin–Induced Platelet Aggregation," *British Journal of Haemathology*, vol. 92:442–451.
Celi, Alessandro, et al., (1997) "Platelet–Leukocyte–Endothelial Cell Interaction On The Blood Vessel Wall," *Seminars in Hematology* vol. 34(4):327–335.
Crommie, Deidre, et al., (1995) "Biosynthesis of GlyCAM–1, a Mucin–Like Ligand for L–Selectin," *The Journal of Biological Chemistry*, vol. 270 (38):22614–22624.
Frenette, Paul S., et al., (1995) "Platelets Roll on Stimulated Endothelium in vivo: An Interaction Mediated By Endothelial P–Selectin," *Proc. Natl. Acad. Sci.*, vol. 92:7450–7454.
Fukuta, Masakazu, et al., (1995) "Molecular Cloning and Expression of Chick Chondrocyte Chondroitin 6–Sulfotransferase," *The Journal of Biological Chemistry*, vol. 270(31):18575–18580.
Fukuta, Masakazu et al., (1997) "Molecular Cloning and Characterization of Human Keratan Sulfate Gal–6–Sulfotransferase," *The Journal of Biological Chemistry*, vol. 272 (51):32321–32328.
Girard, Jean–Philippe, et al., (1995) "High Endothelial Venules (HEVs): Specialized Endothelium For Lymphocyte Migration," *Immunology Today*, vol. 16(9):449–457.
Habuchi, Hiroko, et al., (1998) "Molecular Characterization and Expression of Heparan–sulfate 6–Sulfotransferase," *The Journal of Biological Chemistry*, vol. 273(15):9208–9213.
Habuchi, Osami, et al., (1997) "Sulfation of Sialyl Lactosamine Oligosaccharides By Chondroitin 6–Sulfotransferase," *Gycobiology*, vol. 7 (3):405–412.
Habuchi, Osami, et al., (1996) "Enzymatic Sulfation of Galactose Residue of Keratan Sulfate By Chrondroitin 6–Sulfotransferase," *Glycobiology*, vol. 6(1):51–57.
Habuchi, Osami, et al., (1993) "Purification of Chondroitin 6–Sulfotransferase Secreted from Cultured Chick Embryo Chrondrocytes," *The Journal of Biological Chemistry*, vol. 268, No. (29):21968–21974.

(Continued)

*Primary Examiner*—Manjunath N. Rao
(74) *Attorney, Agent, or Firm*—Paula A. Borden; Bozicevic, Field & Francis LLP

(57) ABSTRACT

A novel human glycosylsulfotransferase expressed in high endothelial cells (GST-3) and polypeptides related thereto, as well as nucleic acid compositions encoding the same, are provided. The subject polypeptides and nucleic acid compositions find use in a variety of applications, including research, diagnostic, and therapeutic agent screening applications. Also provided are methods of inhibiting selectin mediated binding events and methods of treating disease conditions associated therewith.

13 Claims, 7 Drawing Sheets

OTHER PUBLICATIONS

Hemmerich, Stefan, et al., (1995) "Structure of the O–Glycans in GlyCAM–1, An Endothelial–Derived Ligand for L–Selectin," *The Journal of Biological Chemistry*, vol. 270, No. (20):12035–12047.

Hemmerich, Stefan, et al., (1994) "Sulfation–Dependent Recognition of High Endothelial Venules (HEV)–Ligands by L–Selectin and MECA 79, an Adhesion–Blocking Monoclonal Antibody," *The Journal of Experimental Medicine*, vol. 180:2219–2226.

Hemmerich, Stefan, et al., (1994) "6'–Sulfated Sialyl Lewis x Is a Major capping Group of GlyCAM–1," *Biochemistry*, vol. 33, No. (16):4830–4835.

Hemmerich, Stefan, et al., (1994) "Identification of the Sulfated monosaccharides of GlyCAM–1, an Endothelial-Derived Ligand for L–Selectin," *Biochemistry*, vol. 33, No. (16):4820–4829.

Hillier, Marra M., et al., (1996) "The WashU–HHMI Mouse EST Project," *Nucleotide Query*, Accession No. AA522184.

Hooper, Lora V., et al., (1996) "From Legumes to Leukocytes:Biological Roles For Sulfated Carbohydrates," *The FASEB Journal* vol. 10:1137–1146.

Koenig, Andrea, et al., (1997) "Selectin Inhibition: Synthesis and Evaluation of Novel Sialylated, Sulfated and Fucosylated Oligosaccharides, Including The Major Capping Group of GlyCAM–1," *Glycobiology*, vol. 7, No. (1):79–93.

Lasky, Laurence A., et al, (1992) "An Endothelial Ligand for L–Selectin Is a Novel Mucin–Like Molecule," *Cell*, vol. 69:927–938.

Marra et al. (Sep. 12, 1996) Genbank EST database accession No. gb_est15:AA522184.

Mitsuoka, Chikako, et al., (1998) "Identification of a major Carbohydrate Capping Group of the L–selectin Ligand on High Endothelial Venules in Human Lymph Nodes as 6–Sulfo Sialyl Lewis X*," *The Journal of Biological Chemistry*, vol. 273(18):11225–11233.

Robinson et al. (1995) "Singular over–representation of an octameric palindrome, HIP1, in DNA from many cyanobacteria." *Nucleic Acids Research*, vol. 23(5):729–735.

Rosen, Steven D., et al., (1994) "The Selectins and their Ligands," *Current Opinion in Cell Biology*, vol. 6:663–673.

Sawada, Mikiko, et al., (1993) "Specific Expression of a Complex Sialyl Lewis X Antigen on High Endothelial Venules of Human Lymph Nodes: Possible Candidate for L–Selectin Ligand," *Biochemical and Biophysical Research Communications*, vol. 193, No. (1):337–347.

Spiro, Robert G., et al., (1998) "Characterization of a spleen sulphotransferase responsible for the 6–O–sulphation of the galactose residue in sialyl–N–acetyl–lactosamine sequences," *Biochem J.*, vol. 331:265–271.

Tsuboi, Shigeru, et al., (1996) "6'–Sulfo Sialyl $Le^x$ but Not 6–Sulfo Sialyl $Le^x$ Expressed on the Cell Surface Supports L–Selectin–Mediated Adhesion," *The Journal of Biological Chemistry*, vol. 271, No. (44):27213–27216.

Yoshino, Kochichiro, et al., (1997) "Studies on Selectin Blockers. 4. Structure–Function Relationship of Sulfated Sialyl Lewis X Hexasaccharide Ceramides toward E–, P–, and L–Selectin Binding," *J. Med. Chem.*, vol. 40:455–462.

* cited by examiner

FIG. 1

>huGST-3 (from LifeSeq EST #2617407, ORF is highlighted in capitals)

```
gaattccatt gtgttgggta cggaagacga cagaagggta gaggagaaaa gcgcatggcc
cggctagcag tgagcctctc aaaagcagca gggaagccca agccacaagg tcttccactt
cagcacaatg ctactgccta aaaaaATGAA GCTCCTGCTG TTTCTGGTTT CCCAGATGGC
CATCTTGGCT CTATTCTTCC ACATGTACAG CCACAACATC AGCTCCCTGT CTATGAAGGC
ACAGCCCGAG CGCATGCACG TGCTGGTTCT GTCTTCCTGG CGCTCTGGCT CTTCTTTTGT
GGGGCAGCTT TTTGGGCAGC ACCCAGATGT TTTCTACCTG ATGGAGCCCG CCTGGCACGT
GTGGATGACC TTCAAGCAGA GCACCGCCTG GATGCTGCAC ATGGCTGTGC GGGATCTGAT
ACGGGCCGTC TTCTTGTGCG ACATGAGCGT CTTTGATGCC TACATGGAAC CTGGTCCCCG
GAGACAGTCC AGCCTCTTTC AGTGGGAGAA CAGCCGGGCC CTGTGTTCTG CACCTGCCTG
TGACATCATC CCACAAGATG AAATCATCCC CCGGGCTCAC TGCAGGCTCC TGTGCAGTCA
ACAGCCCTTT GAGGTGGTGG AGAAGGCCTG CCGCTCCTAC AGCCACGTGG TGCTCAAGGA
GGTGCGCTTC TTCAACCTGC AGTCCCTCTA CCCGCTGCTG AAAGACCCCT CCCTCAACCT
GCATATCGTG CACCTGGTCC GGGACCCCCG GGCCGTGTTC CGTTCCCGAG AACGCACAAA
GGGAGATCTC ATGATTGACA GTCGCATTGT GATGGGGCAG CATGAGCAAA AACTCAAGAA
GGAGGACCAA CCCTACTATG TGATGCAGGT CATCTGCCAA AGCCAGCTGG AGATCTACAA
GACCATCCAG TCCTTGCCCA AGGCCCTGCA GGAACGCTAC CTGCTTGTGC GCTATGAGGA
CCTGGCTCGA GCCCCTGTGG CCCAGACTTC CCGAATGTAT GAATTCGTGG GATTGGAATT
CTTGCCCCAT CTTCAGACCT GGGTGCATAA CATCACCCGA GGCAAGGGCA TGGGTGACCA
CGCTTTCCAC ACAAATGCCA GGGATGCCCT TAATGTCTCC CAGGCTTGGC GCTGGTCTTT
GCCCTATGAA AAGGTTTCTC GACTTCAGAA AGCCTGTGGC GATGCCATGA ATTTGCTGGG
CTACCGCCAC GTCAGATCTG AACAAGAACA GAGAAACCTG TTGCTGGATC TTCTGTCTAC
CTGGACTGTC CCTGAGCAAA TCCACTAAga gggttgagaa ggctttgctg ccacctggtg
tcagcctcag tcactttctc tgaatgcttc tgagccttgc ctacatctct gagccttaac
tacatgtctg tgggtatcac actgagtgtg agttgtgtcc acacgtgctc aagcagaagg
acttttgtgt ccatgcttgt gtctagaaaa cagactgggg aaccttatgt gagcagcaca
tcccaccagt gaaacagggt attgctcttc ttctttctt gatcttcctg tctgggcaga
cttcagagac tttgtggcct ggaggcctat taagcacgac acagtatcag tggaattgat
ccataaacct ccctgtccac atcttgccca atggggaatg gatctttcac caaagagctc
accagcattt tccacagaga tgcgaattct gagcccttgg agttcccaat gggattcaag
gaaggaagtg ggaacaaggt tggatgccta cttatgagct tgaccataca gctatcggta
atcagaaata tgaaacaaaa tctctgacaa aagagcaagc tcttaagttc acaaggtgcc
tgggcttgat ttgaatatca tttcccttt
```
(SEQ ID NO: 13)

FIG. 2

>huGST-3 (Full length EST Lifeseq #2617407)

```
Met Leu Leu Pro Lys Lys Met Lys Leu Leu Leu Phe Leu Val Ser Gln
1               5                   10                  15
Met Ala Ile Leu Ala Leu Phe Phe His Met Tyr Ser His Asn Ile Ser
            20                  25                  30
Ser Leu Ser Met Lys Ala Gln Pro Glu Arg Met His Val Leu Val Leu
            35                  40                  45
Ser Ser Trp Arg Ser Gly Ser Ser Phe Val Gly Gln Leu Phe Gly Gln
            50                  55                  60
His Pro Asp Val Phe Tyr Leu Met Glu Pro Ala Trp His Val Trp Met
65                      70                  75                  80
Thr Phe Lys Gln Ser Thr Ala Trp Met Leu His Met Ala Val Arg Asp
                85                  90                  95
Leu Ile Arg Ala Val Phe Leu Cys Asp Met Ser Val Phe Asp Ala Tyr
            100                 105                 110
Met Glu Pro Gly Pro Arg Arg Gln Ser Ser Leu Phe Gln Trp Glu Asn
            115                 120                 125
Ser Arg Ala Leu Cys Ser Ala Pro Ala Cys Asp Ile Ile Pro Gln Asp
    130                 135                 140
Glu Ile Ile Pro Arg Ala His Cys Arg Leu Leu Cys Ser Gln Gln Pro
145                 150                 155                 160
Phe Glu Val Val Glu Lys Ala Cys Arg Ser Tyr Ser His Val Val Leu
                165                 170                 175
Lys Glu Val Arg Phe Phe Asn Leu Gln Ser Leu Tyr Pro Leu Leu Lys
            180                 185                 190
Asp Pro Ser Leu Asn Leu His Ile Val His Leu Val Arg Asp Pro Arg
        195                 200                 205
Ala Val Phe Arg Ser Arg Glu Arg Thr Lys Gly Asp Leu Met Ile Asp
    210                 215                 220
Ser Arg Ile Val Met Gly Gln His Glu Gln Lys Leu Lys Lys Glu Asp
225                 230                 235                 240
Gln Pro Tyr Tyr Val Met Gln Val Ile Cys Gln Ser Gln Leu Glu Ile
                245                 250                 255
Tyr Lys Thr Ile Gln Ser Leu Pro Lys Ala Leu Gln Glu Arg Tyr Leu
            260                 265                 270
Leu Val Arg Tyr Glu Asp Leu Ala Arg Ala Pro Val Ala Gln Thr Ser
        275                 280                 285
Arg Met Tyr Glu Phe Val Gly Leu Glu Phe Leu Pro His Leu Gln Thr
    290                 295                 300
Trp Val His Asn Ile Thr Arg Gly Lys Gly Met Gly Asp His Ala Phe
305                 310                 315                 320
His Thr Asn Ala Arg Asp Ala Leu Asn Val Ser Gln Ala Trp Arg Trp
                325                 330                 335
Ser Leu Pro Tyr Glu Lys Val Ser Arg Leu Gln Lys Ala Cys Gly Asp
            340                 345                 350
Ala Met Asn Leu Leu Gly Tyr Arg His Val Arg Ser Glu Gln Glu Gln
        355                 360                 365
Arg Asn Leu Leu Leu Asp Leu Leu Ser Thr Trp Thr Val Pro Glu Gln
    370                 375                 380
Ile His
385             (SEQ ID NO: 2)
```

FIG. 3

>msGST-3 from mouse C57Bl/6 BAC clone #87(b15) (ORF is highlighted as capitals)

```
gggcatctaa cttacacttg gtcagacaag acaagctttt gcctacaaag gccacactct
gtcaggggtg tagaaaggtg tggggtgtgg cagaactccc tatagtgatt aaatgtgctg
ggtaggatat tctcggtggt ttgatggatg agaaagccca gagggtgagt tttaaagact
tgtaacatag aatgcagtga tccaattaag agccagaatt actttgcaga gggatctgga
caaatacttg caggaatgtt tttggttttt gtttgtttgt ttgtttgttt tacattgctc
cttggatggg aatccagaga agcccgaagg tagatgctgt aacaacctaa ctcagcccca
tcccctctgc ttgctctttc aaggtcttct ccttcttccg caggatgatg ctgttgaaga
aagggaggct gctgatgttc ctgggttccc aggtcatcgt tgtagctctc ttcatccata
tgtccgtcca cagacacctt tcccagaggg aggagtccag gaggcccgtg catgtgctgg
tgctgtcttc ctggcggtca ggatcctctt ttgtgggaca gcttttcggg cagcacccgg
atgtgttcta cctgatggag cctgcctggc atgtgtggat gactttcacc agcagcacag
cctggaagct gcacatggct gtgcgggatc ttctgcgttc cgtcttcctg tgtgacatga
gcgtctttga tgcctacatg aacccaggcc ccggaaaca gtccagcctc ttccagtggg
agcaaagccg ggccctgtgc tcagcgcctg tgtgtgactt cttccctgcc cacgagatca
gctcacccaa gcactgcaag ctgctctgcg gtcagcagcc ctttgatatg gtggagaagg
cctgccgctc tcacggcttc gtggtactca aggaggtgcg ttttctcagc ctgcaggccc
tctatccact actcacggac ccttccctca acctgcacgt cgtgcacctg gtccgagacc
cccgggccgt gttccgatcc cgggagcaca ccaccataga actcatggtt gacagtcata
ttgtgctagg gcagcatttg gaaacgatca aggaggaaga ccagccctat tatgccatga
agatcatctg caaaagccag gtggacatag tcaaggccat ccaaaccctc cctgaagctc
tgcagcagcg ctacctgttc ctgaggtatg aggacctggt tcgggcaccc ctggcccaga
cgaccagact atataaattt gtggggttgg atttttttgcc ccacctccaa acatgggttt
acaatgtcac ccgcggcaag ggcatgggtc agcatgcctt ccatactaac gccaggaacg
ccctcaacgt ctctcaggcg tggcgttggt ccttaccttc cgaaaaggtt tcccagcttc
aagatgcctg cggtgaggct atggatttgc tgggatacct ccaggtcaga tctcaacaag
aacaaggcaa cctgtccctg gatcttctgt cctcctccca tatcttgggg caggtcttcc
gagaaggtta aggaggtctg tctgcacccc ttggttccag ccttagtcac cattaaacgc
acagaagcct taaggtataa ccaaactgag tgccccttc tcctcagccc caagcagagg
ggtctttgtg tctatactca tgtctaccct acaactgagc ctaaaaagcc aagaaacagt
atctttctgt cttgaaaata cttaggaacc ttaagcagcc cctttgacct gtcaagcaag
actttcttgt aaccttggcc ttcttacctg tgcataccct ggagactcgg tctggaggca
tactggacac agcaaacagc atctgtggag tgtgtctgta aacctccctg tcacatcttt
tctaag (SEQ ID NO: 14)
```

FIG. 4

```
Met Met Leu Leu Lys Lys Gly Arg Leu Leu Met Phe Leu Gly Ser Gln
1           5               10              15
Val Ile Val Val Ala Leu Phe Ile His Met Ser Val His Arg His Leu
            20              25              30
Ser Gln Arg Glu Glu Ser Arg Arg Pro Val His Val Leu Val Leu Ser
        35              40              45
Ser Trp Arg Ser Gly Ser Ser Phe Val Gly Gln Leu Phe Gly Gln His
    50              55              60
Pro Asp Val Phe Tyr Leu Met Glu Pro Ala Trp His Val Trp Met Thr
65              70              75              80
Phe Thr Ser Ser Thr Ala Trp Lys Leu His Met Ala Val Arg Asp Leu
            85              90              95
Leu Arg Ser Val Phe Leu Cys Asp Met Ser Val Phe Asp Ala Tyr Met
            100             105             110
Asn Pro Gly Pro Arg Lys Gln Ser Ser Leu Phe Gln Trp Glu Gln Ser
        115             120             125
Arg Ala Leu Cys Ser Ala Pro Val Cys Asp Phe Phe Pro Ala His Glu
    130             135             140
Ile Ser Ser Pro Lys His Cys Lys Leu Leu Cys Gly Gln Gln Pro Phe
145             150             155             160
Asp Met Val Glu Lys Ala Cys Arg Ser His Gly Phe Val Val Leu Lys
            165             170             175
Glu Val Arg Phe Leu Ser Leu Gln Ala Leu Tyr Pro Leu Leu Thr Asp
            180             185             190
Pro Ser Leu Asn Leu His Val Val His Leu Val Arg Asp Pro Arg Ala
        195             200             205
Val Phe Arg Ser Arg Glu His Thr Thr Ile Glu Leu Met Val Asp Ser
    210             215             220
His Ile Val Leu Gly Gln His Leu Glu Thr Ile Lys Glu Glu Asp Gln
225             230             235             240
Pro Tyr Tyr Ala Met Lys Ile Ile Cys Lys Ser Gln Val Asp Ile Val
            245             250             255
Lys Ala Ile Gln Thr Leu Pro Glu Ala Leu Gln Gln Arg Tyr Leu Phe
            260             265             270
Leu Arg Tyr Glu Asp Leu Val Arg Ala Pro Leu Ala Gln Thr Thr Arg
        275             280             285
Leu Tyr Lys Phe Val Gly Leu Asp Phe Leu Pro His Leu Gln Thr Trp
    290             295             300
Val Tyr Asn Val Thr Arg Gly Lys Gly Met Gly Gln His Ala Phe His
305             310             315             320
Thr Asn Ala Arg Asn Ala Leu Asn Val Ser Gln Ala Trp Arg Trp Ser
            325             330             335
Leu Pro Tyr Glu Lys Val Ser Gln Leu Gln Asp Ala Cys Gly Glu Ala
            340             345             350
Met Asp Leu Leu Gly Tyr Leu Gln Val Arg Ser Gln Gln Glu Gln Gly
        355             360             365
Asn Leu Ser Leu Asp Leu Leu Ser Ser Ser His Ile Leu Gly Gln Val
    370             375             380
Phe Arg Glu Gly     (SEQ ID NO: 15)
385
```

```
                    106                            134
HEC-GlcNAc6ST   SWRSGSSFVGQLEGQHPDVFYIMEPAWHV
GlcNAc6ST       TWRSGSSFFGELFNQNPEVFFLYEPVWHV
KSGal6ST        TTRSGSSFVGQLFNQHLDVFYLFEPLYHV
C6ST            TTRTGSSFVGEFFNQQGNIFYLFEPIWHI 249              270
HEC-GlcNAc6ST   DPSLNLHIVHLVRDPRAVFRSR
GlcNAc6ST       DPALDLKVIHLVRDPRAVASSR
KSGal6ST        DPRLNLKVLQLVRDPRGILASR
C6ST            DPRLDLRVIQLVRDPRAVLASR 320           339
HEC-GlcNAc6ST   PKALQERYLLVRYEDLARAP   (SEQ ID NO: 16)
GlcNAc6ST       PDWLQGHYLVVRYEDLVGDP   (SEQ ID NO: 17)
KSGal6ST        PPWLKGKYMLVRYEDLARNP   (SEQ ID NO: 18)
C6ST            PAWLRGRYMLVRYEDVARGP   (SEQ ID NO: 19)
```

FIG. 6

GLYCOSYL SULFOTRANSFERASE-3

CROSS-REFERENCE

This application is a continuation of Ser. No. 09/045,284, filed Mar. 20, 1998 now U.S. Pat. No. 6,265,192 B1, Jul. 24, 2001, which is incorporated herein by reference in its entirety and to which application we claim priority.

FIELD OF THE INVENTION

The field of the invention is cell adhesion, particularly selectin mediated cell adhesion, as well as the treatment of disease conditions related thereto.

BACKGROUND OF THE INVENTION

Sulfotransferases are enzymes that catalyze the transfer of a sulfate from a donor compound to an acceptor compound, usually placing the sulfate moiety at a specific location on the acceptor compound. There are a variety of different sulfotransferases which vary in activity, i.e. with respect to the donor and/or acceptor compounds with which they work. Known sulfotransferases include those acting on carbohydrate: heparin/heparan sulfate N-sulfotransferase (NST); chondroitin 6/keratan 6 sulfate sulfotransferase (C6ST/KSST); galactosylceramide 3'-sulfotransferase; heparan sulfate 2-sulfotransferase (Iduronic acid); HNK-1 sulfotransferase (3-glucuronic acid); heparan sulfate D-glucosamino 3-O-sulfotransferase (3-OST); etc., as well as those acting on phenols, steroids and xenobiotics: aryl sulfotransferase I & II, hydroxy-steroid sulfotransferases I, II & III, dehydroepiandrosterone (DHEA); etc. Sulfotransferases play a central role in a variety of different biochemical mechanisms, as the presence of a sulfate moiety on a particular ligand is often required for a particular activity, e.g. binding.

The presence of a sulfate moiety on selectin ligands has been shown to be important for selectin binding to occur. See Imai et al., Nature (1993) 361:555–557 and Imai et al., Glycoconjugate J. (1993) 10:34–39, as well as U.S. Pat. No. 5,695,752. Several selectin ligands have, to date, been identified. The L-selectin endothelial ligands in mouse that have been identified are: CD34, GlyCAM-1, MAdCAM-1 and sgp200. In addition, PSGL-1 has been identified as a leukocyte ligand for P-, E-, and L-selectin. Endothelial ligands for L-selectin in humans are still poorly defined, but include CD34 and podocalyxin.

Selectin mediated binding plays an important and prominent role in a variety of biological processes. Selectins are lectin like cell adhesion molecules that mediate leukocyte-endothelial, leukocyte-leukocyte, leukocyte-platelet, platelet-endothelial and platelet-platelet interactions. One critical biological process in which selectin mediated binding plays a role is the maintenance of immune surveillance.

Maintenance of immune surveillance depends on the constant recirculation of lymphocytes from the blood through the vascular wall into the tissues and eventually back into the blood. Lymphocyte recruitment from the blood into all secondary lymphoid organs (except the spleen) as well as into many sites of chronic inflammation is mediated by a specialized postcapillary venule called a high endothelial venule. These vessels are defined by the distinct, cuboidal morphology of their endothelial cells and their luminal presentation of ligands for the leukocyte adhesion molecule, L-selectin. This lectin-like adhesion molecule is expressed on all classes of leukocytes in the blood and is responsible for the initial tethering and rolling of a leukocyte on the endothelium prior to subsequent integrin mediated firm arrest and transmigration.

Although selectin mediated binding events play a critical role in normal physiological processes, disease conditions do exist for which it is desired to regulate or modulate, e.g. limit or prevent, the amount of selectin mediated binding that occurs. Such conditions include: acute or chronic inflammation; autoimmune and related disorders, tissue rejection during transplantation, and the like.

As the above conditions all result from selectin mediated binding events, there is great interest in the elucidation of the mechanisms underlying such binding events. There is also great interest in the identification of treatment methodologies for these and related disease conditions, as well the identification of active agents for use therein.

As such, there is continued interest in the identification of participants in the selectin binding mechanism, including enzymatic agents, and the elucidation of their role(s) in selectin mediated binding events, as well as the development of therapies for disease conditions arising from such binding events.

Relevant Literature

Chondroitin-6-sulfotransferase is disclosed in EP 821 066, as well as in Fukuta et al., "Molecular Cloning and Characterization of Human Keratan Sulfate Gal-6-Sulfotransferase," J. Biol. Chem. (Dec. 19, 1997) 272: 32321–32328; Habuchi et al., "Enzymatic Sulfation of Galactose Residue of Keratan Sulfate by Chondroitin 6-Sulfotransferase," Glycobiology (January 1996) 6:51–57; Habuchi et al., "Enzymatic Sulfation of Galactose Residue of Keratan Sulfate by Chondroitin 6-Sulfate by Chondroitin 6-Sulfotransferase," Glycobiology (January 1996) 6:51–57; Fukuta et al., "Molecular Cloning and Expression of Chick Chondrocyte Chondroitin 6-Sulfotransferase," J. Biol. Chem. (1995) 270: 18575–18580; and Habuchi et al., "Purification of Chondroitin 6-Sulfotransferase Secreted from Cultured Chick Embryo Chondrocytes," J. Biol. Chem. (1993) 268: 21968–21974.

References providing background information on selectin mediated binding include: Baumhueter et al., "Binding of L-Selectin to the Vascular Sialomucin CD34," Science (Oct. 15, 1993): 436–438; Boukerche et al., "A Monoclonal Antibody Directed Against a Granule Membrane Glycoprotein (GMP-140/PADGEM, P-selectin, CD62P) Inhibits Ristocetin-Induced Platelet Aggregation," Br. J. Haematology (1996) 92: 442–451; Celi et al., "Platelet-Leukocyte-Endothelial Cell Interaction on the Blood Vessel Wall," Seminars in Hematology (1997) 34: 327–335; Frenette et al., "Platelets Roll on Stimulated Endothelium In Vivo: An Interaction Mediated by Endothelial P-selectin," Proc. Natl. Acad. Sci. USA (August 1995) 52:7450–7454; Girard & Springer, "High Endothelial Venules (HEVs): Specialized Endothelium for Lymphocyte Migration," Immun. Today (1995) 16: 449–457; Hemmerich et al., "Sulfation Dependent Recognition of High Endothelial Venules (HEV)-Ligands by L-Selectin and Meca79, and Adhesion-Blocking Monoclonal Antibody," J. Exp. Medicine (December 1994) 180: 2219–2226; 262 Lasky et al., "An Endothelial Ligand for L-Selectin Is a Novel Mucin-Like Molecule," Cell (Jun. 12, 1992) 69:927–938; Rosen & Bertozzi, "The Selectins and Their Ligands," Current Opinion in Cell Biology (1994) 6: 663–673; and Sawada et al., "Specific Expression of a Complex Sialyl Lewis X Antigen On High Endothelial Venules of Human Lymph Nodes: Possible Candidate for L-selectin Ligand," Biochem. Biophys. Res. Comm. (May 28, 1993) 193: 337–347; as well as U.S. Pat. No. 5,580,862.

U.S. Pat. No. 5,695,752 describes methods of treating inflammation through administration of sulfation inhibitors.

SUMMARY OF THE INVENTION

A novel human glycosyl sulfotransferase (GST-3) and polypeptides related thereto, as well as nucleic acid compositions encoding the same, are provided. The subject polypeptide and nucleic acid compositions find use in a variety of applications, including research, diagnostic, and therapeutic agent screening applications, as well as in treatment therapies. Also provided are methods of inhibiting selectin mediated binding events and methods of treating disease conditions associated therewith.

BRIEF DESCRIPTION OF THE FIGURES

FIG. 1 provides the cDNA sequence of Human GST-3, where the open reading frame is highlighted in capital letters. The sequence represented in FIG. 1 is SEQ ID NO:01.

FIG. 2 provides the amino acid sequence of human GST-3.

FIG. 3 provides a representation of the derivation of primers that were employed in homology PCR on HEV-cDNA. Peptide sequences GST-1 and GST-2 were aligned with several known sulfotransferases retrieved from the Genbank database using the ClustalW (Thompson et al., Nuc. Acids Res. (1994) 22: 4673–4680) algorithm. Three consensus regions A, B, & C were identified. These are depicted above in order 5' to 3' (N-terminal to C-terminal) with the intermittent and flanking regions of less or no homology truncated. Highly degenerate forward primers A+ and B+ and reverse primers B– and C– containing toggle bases as well as inosine were designed as decribed in the experimental section. These primers encode a maximal number of permutations at the amino-acid level in order to accomodate most patterns highlighted above in red or brown.

FIG. 4 provides a representation of the results obtained from fractionation PCR products generated using the primers of FIG. 3. Two rounds of homology PCR with the above degenerate primers were performed on HEV-cDNA as described in the experimental section. The primer combinations used were A+ with B– and B+ with C–. The products of the second round were fractionated through 1% agarose and indicated bands excised and subcloned for sequencing (X: reaction on HEV-cDNA template; O; no template control). Four sequences derived from band 2.2 were found to map to an EST homologous to GST-1 and 2 listed in the private Incyte database. All other sequences neither encode an open reading frame nor score any statistically significant matches when used as query sequences in BLAST database searches.

FIG. 6 provides a representation of the protein domain structure of C6ST/KSST and GST-1, GST-2 and GST-3.

DETAILED DESCRIPTION OF THE INVENTION

Figure 5:
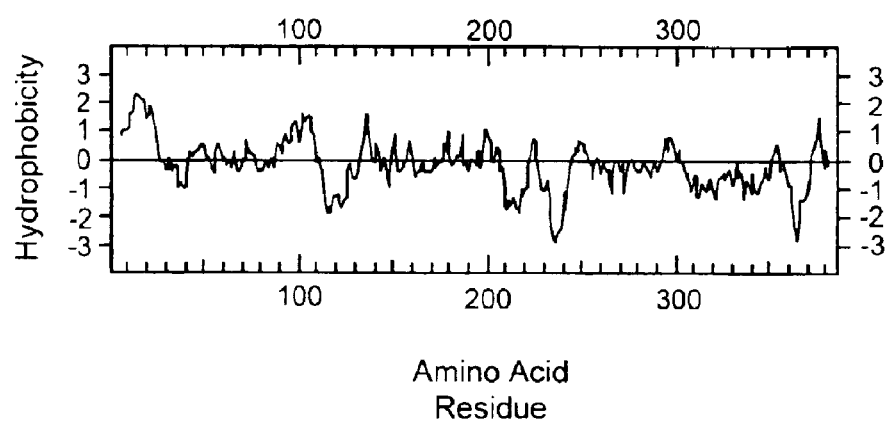
FIG. 5 is a representation demonstrating that GST-3 is expressed in HEC, but not HUVEC or lymphocytes. Primers specific for GST 3 were used to amplify a 500 bp PCR fragment from HEC cDNA. The input cDNA was varied in two-fold dilution steps from left to right. A PCR product is detected from HEC cDNA at dilutions up to 1:8. No PCR product was amplified from human lymphocyte or HUVEC cDNAs at any dilution of the cDNAs. Amplification of HPRT (a ubiquitously expressed "house keeping enzyme") indicates that none of the cDNAs were substantially degraded and similar amounts of template were present in each set of reactions.

A novel human glycosyl transferase expressed in high endothelial cells (HEC) and polypeptides related thereto, as well as nucleic acid compositions encoding the same, are provided. The subject polypeptide and/or nucleic acid compositions find use in a variety of different applications, including research, diagnostic, and therapeutic agent screening/discovery/preparation applications. Also provided are methods of inhibiting selectin mediated binding events and methods of treating disease conditions associated therewith.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

Polypeptide Compositions

A novel human glycosylsulfotransferase expressed in high endothelial cells (HEC), as well as polypeptide compositions related thereto, are provided. The term polyeptide composition as used herein refers to both the full length human protein as well as portions or fragments thereof. Also included in this term are variations of the naturally occurring human protein, where such variations are homologous or substantially similar to the naturally occurring protein, as described in greater detail below, as well as corresponding homologs from non-human species, such as other mammalian species. In the following description of the subject invention, the term GST-3 is used to refer not only to the human form of this novel sulfotransferase, but also to homologs thereof expressed in non-human species.

The novel human glycosylsulfotransferase enzyme of the subject invention has been named human glycosyl sulfotransferase 3 or huGST-3. huGST-3 is a type 2 membrane protein having a relatively short transmembrane domain and a short amino-terminal cytoplasmic tail. huGST-3 has a 31% amino acid sequence identity with CS6T/KSST (Habuchi et al., J. Biol. Chem. (1995) 240:4172–4179) as measured by using the "GAP" program (part of the Wisconsin Sequence Analysis Package available through the Genetics Computer Group, Inc. (Madison Wis.)), where the parameters are: Gap weight: 12; length wieght:4. huGST-3 is capable of sulfating selectin ligands, particularly L-selectin ligands, e.g. GlyCAM-1. By sulfating selectin ligands is meant that huGST-3 is capable of catalyzing the transfer of a sulfate group from a donor compound to a position on a selectin ligand precursor as acceptor compound. Donor compounds from which huGST-3 obtains sulfate groups for transfer to acceptor ligand compounds include 3'-phosphoadenosine 5'-phosphosulfate (PAPS) and the like. Selectin ligands capable of being sulfated through huGST-3 action include E-, P- and L-selectin ligands, particularly L-selectin ligands, such as GlyCAM-1, CD34, MAdCAM-1, Sgp200, podocalyxin, and the like. huGST-3 is strongly predicted to have Gal-6-O sulfotransferase activity.

Human GST-3 is a 386 amino acid protein having an amino acid sequence as shown in FIG. 2 and identified as SEQ ID NO:02. huGST-3 has a molecular weight based on its amino acid of about 45 kDa to 46 kDa, and more specifically from about 45100 to 45200 dalton, and specifically 45104 dalton (using DNA Strider 1.2 software). Since GST-3 is glycosylated, its true molecular weight is greater, and is likely to be in the range from about 45 to 85 kDa, and more likely from about 50 kDa to 65 kDa. Expression of GST-3 in humans is highly restricted. For example, huGST-3 is expressed in HEC but not tonsillar lymphocytes, or primary cultured human umbilical vein endothelial cells (HUVEC).

In addition to the huGST-3, also provided are GST-3 proteins that are have the same expression pattern in humans and huGST-3, i.e. are highly restricted and expressed in HEC but not HUVEC or lymphocytes. huGST-3 homologs or proteins (or fragments thereof) from nonhuman species are also provided, including mammals, such as: rodents, e.g. mice, rats; domestic animals, e.g. horse, cow, dog, cat; and humans, as well as non-mammalian species, e.g. avian, and the like. By homolog is meant a protein having at least about 35%, usually at least about 40% and more usually at least about 60% amino acid sequence identity to the huGST-3 protein.

Also provided are GST-3 proteins that are substantially identical to the huGST-3 protein, where by substantially identical is meant that the protein as an amino acid sequence identity to the sequence of huGST-3 of at least about 35%, usually at least about 40% and more usually at least about 60%.

The GST-3 proteins of the subject invention (e.g. huGST-3 or a homolog thereof) are present in a non-naturally occurring environment, e.g. are separated from their naturally occurring environment. In certain embodiments, the subject GST-3 is present in a composition that is enriched for GST-3 as compared to GST-3 in its naturally occurring environment. As such, purified GST-3 is provided, where by purified is meant that GST-3 is present in a composition that is substantially free of non-GST-3 proteins, where by substantially free is meant that less than 90%, usually less than 60% and more usually less than 50% of the composition is made up of non-GST-3 proteins. The GST-3 of the subject invention may also be present as an isolate, by which is meant that the GST-3 is substantially free of both non-GST-3 proteins and other naturally occurring biologic molecules, such as oligosaccharides, polynucleotides and fragments thereof, and the like, where substantially free in this instance means that less than 70%, usually less than 60% and more usually less than 50% of the composition containing the isolated GST-3 is a non-GST-3 naturally occurring biological molecule. In certain embodiments, the GST-3 is present in substantially pure form, where by substantially pure form is meant at least 95%, usually at least 97% and more usually at least 99% pure.

In addition to the naturally occurring GST-3 protein, GST-3 polypeptides which vary from the naturally occurring GST-3 protein are also provided. By GST-3 polypeptide is meant an amino acid sequence encoded by an open reading frame (ORF) of the GST-3 gene, described in greater detail below, including the full length GST-3 protein and fragments thereof, particularly biologically active fragments and/or fragments corresponding to functional domains, e.g. acceptor binding site (postulated to be the most 5' consensus region A (see experimental section infra), the donor binding site, e.g. VRYEDL, (SEQ ID NO:09), and the like; and including fusions of the subject polypeptides to other proteins or parts thereof. Fragments of interest will typically be at least about 10 aa in length, usually at least about 50 aa in length, and may be as long as 300 aa in length or longer, but will usually not exceed about 1000 aa in length, where the fragment will have a stretch of amino acids that is identical to GST-3 of at least about 10 aa, and usually at least about 15 aa, and in many embodiments at least about 50 aa in length.

The subject GST-3 proteins and polypeptides may be obtained from naturally occurring sources or synthetically produced. Where obtained from naturally occurring sources, the source chosen will generally depend on the species from which the GST-3 is to be derived. For example, huGST-3 is generally derived from endothelial cells of high endothelial venules (HEV) of human secondary lymphoid organs, such as tonsils. The subject GST-3 may also be derived from synthetic means, e.g. by expressing a recombinant gene encoding GST-3 in a suitable host, as described in greater detail below. Any convenient protein purification procedures may be employed, where suitable protein purification methodologies are described in Guide to Protein Purification, (Deuthser ed.) (Academic Press, 1990). For example, a lysate may prepared from the original source, e.g. HEC or the expression host, and purified using HPLC, exclusion chromatography, gel electrophoresis, affinity chromatography, and the like.

Nucleic Acid Compositions

Also provided are nucleic acid compositions encoding GST-3 proteins or fragments thereof. By nucleic acid composition is meant a composition comprising a sequence of DNA having an open reading frame that encodes GST-3, i.e. a GST-3 gene, and is capable, under appropriate conditions, of being expressed as GST-3. Also encompassed in this term are nucleic acids that are homologous or substantially similar or identical to the nucleic acids encoding GST-3 proteins. Thus, the subject invention provides genes encoding huGST-3 and homologs thereof. The human GST-3 gene has the nucleic acid sequence shown in FIG. 1 and identified as SEQ ID NO:01, infra.

The source of homologous genes may be any species, e.g., primate species, particularly human; rodents, such as rats and mice, canines, felines, bovines, ovines, equines, yeast, nematodes, etc. Between mammalian species, e.g., human and mouse, homologs have substantial sequence similarity, e.g. at least 75% sequence identity, usually at least 90%, more usually at least 95% between nucleotide sequences. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990), *J. Mol. Biol.* 215:403–10 (using default settings). The sequences provided herein are essential for recognizing GST-3-related and homologous proteins in database searches.

Nucleic acids encoding the GST-3 protein and GST-3 polypeptides of the subject invention may be cDNA or genomic DNA or a fragment thereof. The term "GST-3 gene" shall be intended to mean the open reading frame encoding specific GST-3 proteins and polypeptides, and GST-3 introns, as well as adjacent 5' and 3' non-coding nucleotide sequences involved in the regulation of expression, up to about 20 kb beyond the coding region, but possibly further in either direction. The gene may be introduced into an appropriate vector for extrachromosomal maintenance or for integration into a host genome.

The term "cDNA" as used herein is intended to include all nucleic acids that share the arrangement of sequence elements found in native mature mRNA species, where sequence elements are exons and 3' and 5' non-coding regions. Normally mRNA species have contiguous exons, with the intervening introns, when present, being removed by nuclear RNA splicing, to create a continuous open reading frame encoding a GST-3 protein.

A genomic sequence of interest comprises the nucleic acid present between the initiation codon and the stop codon, as defined in the listed sequences, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence. The genomic DNA flanking the coding region, either 3' or 5', or internal regulatory sequences as sometimes found in introns, contains sequences required for proper tissue and stage specific expression.

The nucleic acid compositions of the subject invention may encode all or a part of the subject GST-3 protein. Double or single stranded fragments may be obtained from the DNA sequence by chemically synthesizing oligonucleotides in accordance with conventional methods, by restriction enzyme digestion, by PCR amplification, etc. For the most part, DNA fragments will be of at least 15 nt, usually at least 18 nt or 25 nt, and may be at least about 50 nt.

The GST-3 genes are isolated and obtained in substantial purity, generally as other than an intact chromosome. Usually, the DNA will be obtained substantially free of other nucleic acid sequences that do not include a GST-3 sequence or fragment thereof, generally being at least about 50%, usually at least about 90% pure and are typically "recombinant", i.e. flanked by one or more nucleotides with which it is not normally associated on a naturally occurring chromosome.

Preparation of GST-3 Polypeptides

In addition to the plurality of uses described in greater detail in following sections, the subject nucleic acid compositions find use in the preparation of all or a portion of the GST-3 polypeptides, as described above. For expression, an expression cassette may be employed. The expression vector will provide a transcriptional and translational initiation region, which may be inducible or constitutive, where the coding region is operably linked under the transcriptional control of the transcriptional initiation region, and a transcriptional and translational termination region. These control regions may be native to a GST-3 gene, or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for the production of fusion proteins, where the exogenous fusion peptide provides additional functionality, i.e. increased protein synthesis, stability, reactivity with defined antisera, an enzyme marker, e.g. -galactosidase, etc.

Expression cassettes may be prepared comprising a transcription initiation region, the gene or fragment thereof, and a transcriptional termination region. Of particular interest is the use of sequences that allow for the expression of functional epitopes or domains, usually at least about 8 amino acids in length, more usually at least about 15 amino acids in length, to about 25 amino acids, and up to the complete open reading frame of the gene. After introduction of the DNA, the cells containing the construct may be selected by means of a selectable marker, the cells expanded and then used for expression.

GST-3 proteins and polypeptides may be expressed in prokaryotes or eukaryotes in accordance with conventional ways, depending upon the purpose for expression. For large scale production of the protein, a unicellular organism, such as *E. coli, B. subtilis, S. cerevisiae*, insect cells in combination with baculovirus vectors, or cells of a higher organism such as vertebrates, particularly mammals, e.g. COS 7 cells, may be used as the expression host cells. In some situations, it is desirable to express the GST-3 gene in eukaryotic cells, where the GST-3 protein will benefit from native folding and post-translational modifications. Small peptides can also be synthesized in the laboratory. Polypeptides that are subsets of the complete GST-3 sequence may be used to identify and investigate parts of the protein important for function.

Uses of the Subject GST-3 Polypeptide and Nucleic Acid Compositions

The subject polypeptide and nucleic acid compositions find use in a variety of different applications, including research, diagnostic, and therapeutic agent screening/discovery/preparation applications, as well as therapeutic compositions.

Research Applications

The subject nucleic acid compositions find use in a variety of research applications. Research applications of interest include: the identification of huGST-3 homologs; as a source of novel promoter elements; the identification of GST-3 expression regulatory factors; as probes and primers in hybridization applications, e.g. PCR; the identification of expression patterns in biological specimens; the preparation of cell or animal models for GST-3 function; the preparation of in vitro models for GST-3 function; etc.

Homologs of GST-3 are identified by any of a number of methods. A fragment of the provided cDNA may be used as a hybridization probe against a cDNA library from the target organism of interest, where low stringency conditions are used. The probe may be a large fragment, or one or more short degenerate primers. Nucleic acids having sequence similarity are detected by hybridization under low stringency conditions, for example, at 50° C. and 6XSSC (0.9 M sodium chloride/0.09 M sodium citrate) and remain bound when subjected to washing at 55° C. in 1XSSC (0.15 M sodium chloride/0.015 M sodium citrate). Sequence identity may be determined by hybridization under stringent conditions, for example, at 50° C. or higher and 0.1XSSC (15 mM sodium chloride/01.5 mM sodium citrate). Nucleic acids having a region of substantial identity to the provided GST-3 sequences, e.g. allelic variants, genetically altered versions of the gene, etc., bind to the provided GST-3 sequences under stringent hybridization conditions. By using probes, particularly labeled probes of DNA sequences, one can isolate homologous or related genes.

The sequence of the 5' flanking region may be utilized for promoter elements, including enhancer binding sites, that provide for developmental regulation in tissues where GST-3 is expressed. The tissue specific expression is useful for determining the pattern of expression, and for providing promoters that mimic the native pattern of expression. Naturally occurring polymorphisms in the promoter region are useful for determining natural variations in expression, particularly those that may be associated with disease.

Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al. (1995), *Mol. Med.* 1:194–205; Mortlock et al. (1996), *Genome Res.* 6:327–33; and Joulin and Richard-Foy (1995), *Eur. J. Biochem.* 232:620–626.

The regulatory sequences may be used to identify cis acting sequences required for transcriptional or translational regulation of GST-3 expression, especially in different tissues or stages of development, and to identify cis acting sequences and trans-acting factors that regulate or mediate GST-3 expression. Such transcription or translational control regions may be operably linked to a GST-3 gene in order to promote expression of wild type or altered GST-3 or other proteins of interest in cultured cells, or in embryonic, fetal or adult tissues, and for gene therapy.

Small DNA fragments are useful as primers for PCR, hybridization screening probes, etc. Larger DNA fragments, i.e. greater than 100 nt are useful for production of the encoded polypeptide, as described in the previous section. For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The DNA may also be used to identify expression of the gene in a biological specimen. The manner in which one probes cells for the presence of particular nucleotide sequences, as genomic DNA or RNA, is well established in the literature. Briefly, DNA or mRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to the subject sequence is indicative of GST-3 gene expression in the sample.

The sequence of a GST-3 gene, including flanking promoter regions and coding regions, may be mutated in various ways known in the art to generate targeted changes in promoter strength, sequence of the encoded protein, etc. The DNA sequence or protein product of such a mutation will usually be substantially similar to the sequences provided herein, i.e. will differ by at least one nucleotide or amino acid, respectively, and may differ by at least two but not more than about ten nucleotides or amino acids. The sequence changes may be substitutions, insertions, deletions, or a combination thereof. Deletions may further include larger changes, such as deletions of a domain or exon. Other modifications of interest include epitope tagging, e.g. with the FLAG system, HA, etc. For studies of subcellular localization, fusion proteins with green fluorescent proteins (GFP) may be used.

Techniques for in vitro mutagenesis of cloned genes are known. Examples of protocols for site specific mutagenesis may be found in Gustin et al. (1993), *Biotechniques* 14:22; Barany (1985), *Gene* 37:111–23; Colicelli et al. (1985), *Mol. Gen. Genet.* 199:537–9; and Prentki et al. (1984), *Gene* 29:303–13. Methods for site specific mutagenesis can be found in Sambrook et al., *Molecular Cloning: A Laboratory Manual*, CSH Press 1989, pp. 15.3–15.108; Weiner et al. (1993), *Gene* 126:35–41; Sayers et al. (1992), *Biotechniques* 13:592–6; Jones and Winistorfer (1992), *Biotechniques* 12:528–30; Barton et al. (1990), *Nucleic Acids Res* 18:7349–55; Marotti and Tomich (1989), *Gene Anal. Tech.* 6:67–70; and Zhu (1989), *Anal Biochem* 177:120–4. Such mutated genes may be used to study structure-function relationships of GST-3, or to alter properties of the protein that affect its function or regulation.

The subject nucleic acids can be used to generate transgenic, non-human animals or site specific gene modifications in cell lines. Transgenic animals may be made through homologous recombination, where the normal gst-3 locus is altered. Alternatively, a nucleic acid construct is randomly integrated into the genome. Vectors for stable integration include plasmids, retroviruses and other animal viruses, YACs, and the like.

The modified cells or animals are useful in the study of gst-3 function and regulation. For example, a series of small deletions and/or substitutions may be made in the host's native gst-3 gene to determine the role of different exons in oncogenesis, signal transduction, etc. Of interest are the use of gst-3 to construct transgenic animal models for cancer, where expression of GST-3 is specifically reduced or absent. Specific constructs of interest include anti-sense gst-3, which will block GST-3 expression, expression of dominant negative gst-3 mutations, and over-expression of GST-3 genes. Where a gst-3 sequence is introduced, the introduced sequence may be either a complete or partial sequence of a gst-3 gene native to the host, or may be a complete or partial gst-3 sequence that is exogenous to the host animal, e.g., a human GST-3 sequence. A detectable marker, such as lac Z may be introduced into the gst-3 locus, where upregulation of gst-3 expression will result in an easily detected change in phenotype.

One may also provide for expression of the gst-3 gene or variants thereof in cells or tissues where it is not normally expressed, at levels not normally present in such cells or tissues, or at abnormal times of development.

DNA constructs for homologous recombination will comprise at least a portion of the human GST-3 gene or of a gst-3 gene native to the species of the host animal, wherein the gene has the desired genetic modification(s), and includes regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. (1990), *Meth. Enzymol.* 185:527–537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of leukemia inhibiting factor (LIF). When ES or embryonic cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting offspring screened for the construct. By providing for a different phenotype of the blastocyst and the genetically modified cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture. The transgenic animals may be any non-human mammal, such as laboratory animals, domestic animals, etc. The transgenic animals may be used in functional studies, drug screening, etc., e.g. to determine the effect of a candidate drug on GST-3 activity.

The availability of a number of components in the leukocyte trafficking mechanism, such as GlyCAM-1, L-selectin and the subject GST-3 enzyme, and the like, allows in vitro reconstitution of the mechanism, i.e. the production of an in vitro model.

Diagnostic Applications

Also provided are methods of diagnosing disease states based on observed levels of GST-3 or the expression level of the GST-3 gene in a biological sample of interest. Samples, as used herein, include biological fluids such as semen, blood, cerebrospinal fluid, tears, saliva, lymph, dialysis fluid and the like; organ or tissue culture derived fluids; and fluids extracted from physiological tissues. Also included in the term are derivatives and fractions of such fluids. The cells may be dissociated, in the case of solid tissues, or tissue sections may be analyzed. Alternatively a lysate of the cells may be prepared.

A number of methods are available for determining the expression level of a gene or protein in a particular sample. Diagnosis may be performed by a number of methods to determine the absence or presence or altered amounts of normal or abnormal GST-3 in a patient sample. For example, detection may utilize staining of cells or histological sections with labeled antibodies, performed in accordance with conventional methods. Cells are permeabilized to stain cytoplasmic molecules. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Alternatively, the secondary antibody conjugated to a flourescent compound, e.g. fluorescein, rhodamine, Texas red, etc. Final detection uses a substrate that undergoes a color change in the presence of the peroxidase. The absence or presence of antibody binding may be determined by various methods, including flow cytometry of dissociated cells, microscopy, radiography, scintillation counting, etc.

Alternatively, one may focus on the expression of GST-3. Biochemical studies may be performed to determine whether a sequence polymorphism in a GST-3 coding region or control regions is associated with disease. Disease associated polymorphisms may include deletion or truncation of the gene, mutations that alter expression level, that affect the activity of the protein, etc.

Changes in the promoter or enhancer sequence that may affect expression levels of GST-3 can be compared to expression levels of the normal allele by various methods known in the art. Methods for determining promoter or enhancer strength include quantitation of the expressed natural protein; insertion of the variant control element into a vector with a reporter gene such as β-galactosidase, luciferase, chloramphenicol acetyltransferase, etc. that provides for convenient quantitation; and the like.

A number of methods are available for analyzing nucleic acids for the presence of a specific sequence, e.g. a disease associated polymorphism. Where large amounts of DNA are available, genomic DNA is used directly. Alternatively, the region of interest is cloned into a suitable vector and grown in sufficient quantity for analysis. Cells that express GST-3 may be used as a source of mRNA, which may be assayed directly or reverse transcribed into cDNA for analysis. The nucleic acid may be amplified by conventional techniques, such as the polymerase chain reaction (PCR), to provide sufficient amounts for analysis. The use of the polymerase chain reaction is described in Saiki, et al. (1985), *Science* 239:487, and a review of techniques may be found in Sambrook, et al. *Molecular Cloning: A Laboratory Manual*, CSH Press 1989, pp. 14.2–14.33. Alternatively, various methods are known in the art that utilize oligonucleotide ligation as a means of detecting polymorphisms, for examples see Riley et al. (1990), *Nucl. Acids Res.* 18:2887–2890; and Delahunty et al. (1996), *Am. J. Hum. Genet.* 58:1239–1246.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}$P, $^{35}$S, $^{3}$H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified or cloned fragment, is analyzed by one of a number of methods known in the art. The nucleic acid may be sequenced by dideoxy or other methods, and the sequence of bases compared to a wild-type GST-3 sequence. Hybridization with the variant sequence may also be used to determine its presence, by Southern blots, dot blots, etc. The hybridization pattern of a control and variant sequence to an array of oligonucleotide probes immobilized on a solid support, as described in U.S. Pat. No. 5,445,934, or in WO 95/35505, may also be used as a means of detecting the presence of variant sequences. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. Alternatively, where a polymorphism creates or destroys a recognition site for a restriction endonuclease, the sample is digested with that endonuclease, and the products size fractionated to determine whether the fragment was digested. Fractionation is performed by gel or capillary electrophoresis, particularly acrylamide or agarose gels.

Screening for mutations in GST-3 may be based on the functional or antigenic characteristics of the protein. Protein truncation assays are useful in detecting deletions that may affect the biological activity of the protein. Various immunoassays designed to detect polymorphisms in GST-3 proteins may be used in screening. Where many diverse genetic mutations lead to a particular disease phenotype, functional protein assays have proven to be effective screening tools. The activity of the encoded GST-3 protein may be determined by comparison with the wild-type protein.

Diagnostic methods of the subject invention in which the level of GST-3 expression is of interest will typically involve comparison of the GST-3 nucleic acid abundance of a sample of interest with that of a control value to determine any relative differences, where the difference may be measured qualitatively and/or quantitatively, which differences are then related to the presence or absence of an abnormal GST-3 expression pattern. A variety of different methods for determine the nucleic acid abundance in a sample are known to those of skill in the art, where particular methods of interest include those described in: Pietu et al., Genome Res. (June 1996) 6: 492–503; Zhao et al., Gene (Apr. 24, 1995) 156: 207–213; Soares, Curr. Opin. Biotechnol. (October 1997) 8: 542–546; Raval, J. Pharmacol Toxicol Methods (November 1994) 32: 125–127; Chalifour et al., Anal. Biochem (February 1, 1994) 216: 299–304; Stolz & Tuan, Mol. Biotechnol. (December 19960 6: 225–230; Hong et al., Bioscience Reports (1982) 2: 907; and McGraw, Anal. Biochem. (1984) 143: 298. Also of interest are the methods disclosed in WO 97/27317, the disclosure of which is herein incorporated by reference.

Screening Assays

The subject GST-3 polypeptides find use in various screening assays designed to identify therapeutic agents. Thus, one can use a cell model such as a host cell, e.g. COS7 cell, which has been cotransfected with a selectin ligand cDNA, e.g. GlyCAM-1 and a GST-3 vector. One can then label the transfectants with a labeled sulfate, e.g. $^{35}$S-labeled sulfate, and compare the amount of sulfate incorporation into GlyCAM-1 in the presence and absence of a candidate inhibitor compound. Alternatively, in a cell-free enzyme activity assay, recombinant GST-3 polypeptide may be combined with $^{35}$S-labeled sulfate donor such as [$^{35}$S]-PAPS, candidate inhibitor compound, and an acceptor molecule, which may be a synthetic carbohydrate mimicking structures found in mature and/or immature L-selectin ligands, or a simple nucleophile capable of accepting sulfate (such as phenolic compunds, and the like). The amount of [$^{35}$S]-sulfate transferred to the receptor by the candidate agent is then determined by counting the acceptor-associated radio-activity or product quantitation with an antibody specific for the sulfated acceptor, or in a suitable scintillation proximity assay format. Alternatively, the candidate inhibitor compound may also be combined with a selectin, a non-sulfated selectin ligand precursor, GST-3 and a sulfate donor compound under physiological conditions and the resultant amount of ligand which is capable of binding to the selectin is determined. Depending on the particular method, one or more of, usually one of, the specified components may be labeled, where by labeled is meant that the components comprise a detectable moiety, e.g. a fluorescent or radioactive tag, or a member of a signal producing system, e.g. biotin for binding to an enzyme-streptavidin conjugate in which the enzyme is capable of converting a substrate to a chromogenic product.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used.

The above screening methods may be designed a number of different ways, where a variety of assay configurations and protocols may be employed, as are known in the art. For example, one of the components may be bound to a solid support, and the remaining components contacted with the support bound component. The above components of the method may be combined at substantially the same time or at different times. Incubations are performed at any suitable temperature, typically between 4 and 40° C. Incubation periods are selected for optimum activity, but may also be optimized to facilitate rapid high-throughput screening. Typically between 0.1 and 1 hours will be sufficient. Following the contact and incubation steps, the subject methods will generally, though not necessarily, further include a washing step to remove unbound components, where such a washing step is generally employed when required to remove label that would give rise to a background signal during detection, such as radioactive or fluorescently labeled non-specifically bound components. Following the optional washing step, the presence of bound selectin-ligand complexes will then be detected.

A variety of different candidate agents may be screened by the above methods. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

GST-3 Nucleic Acid and Polypeptide Therapeutic Compositions

The nucleic acid compositions of the subject invention also find use as therapeutic agents in situations where one wishes to enhance GST-3 activity in a host. The GST-3 genes, gene fragments, or the encoded GST-3 protein or protein fragments are useful in gene therapy to treat disorders associated with GST-3 defects. Expression vectors may be used to introduce the GST-3 gene into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

The gene or GST-3 protein may be introduced into tissues or host cells by any number of routes, including viral infection, microinjection, or fusion of vesicles. Jet injection may also be used for intramuscular administration, as described by Furth et al. (1992), *Anal Biochem* 205:365–368. The DNA may be coated onto gold microparticles, and delivered intradermally by a particle bombardment device, or "gene gun" as described in the literature (see, for example, Tang et al. (1992), *Nature* 356:152–154), where gold microprojectiles are coated with the DNA, then bombarded into skin cells.

Methods of Modulating Selectin Mediated Binding Events

Also provided are methods of regulating, including modulating and inhibiting, selectin mediated binding events. The selectin receptor of the selectin mediated binding event will generally be a receptor which binds to a sulfated ligand under physiological conditions and is a member of the selectin family of receptors that have an amino terminal C-type lectin domain followed by an EFG-like domain, a variable number of short consensus repeats known as SCR, CRP or sushi domains, and share greater than 50% homology in their lectin and EFG domains. Of interest is the modulation of selectin binding events in which the selectin is L-, P-, or E-selectin. Of particular interest are L-selecting mediated binding events.

Where the selectin mediated binding event occurs in vivo in a host, an effective amount of active agent that modulates the activity, usually reduces the activity, of GST-3 in vivo, is administered to the host. The active agent may be a variety of different compounds, including a naturally occurring or synthetic small molecule compound, an antibody, fragment or derivative thereof, an antisense composition, and the like.

Naturally occurring or synthetic small molecule compounds of interest include numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Also of interest as active agent are antibodies that at least reduce, if not inhibit, GST-3 activity in the host. Suitable antibodies are obtained by immunizing a host animal with peptides comprising all or a portion of GST-3 protein. Suitable host animals include mouse, rat sheep, goat, hamster, rabbit, etc. The origin of the protein immunogen may be mouse, human, rat, monkey etc. The host animal will generally be a different species than the immunogen, e.g. human GST-3 used to immunize mice, etc.

The immunogen may comprise the complete protein, or fragments and derivatives thereof. Preferred immunogens comprise all or a part of GST-3, where these residues contain the post-translation modifications, such as glycosylation, found on the native GST-3. Immunogens comprising the extracellular domain are produced in a variety of ways known in the art, e.g. expression of cloned genes using conventional recombinant methods, isolation from HEC, etc.

For preparation of polyclonal antibodies, the first step is immunization of the host animal with GST-3, where the GST-3 will preferably be in substantially pure form, comprising less than about 1% contaminant. The immunogen may comprise complete GST-3, fragments or derivatives thereof. To increase the immune response of the host animal, the GST-3 may be combined with an adjuvant, where suitable adjuvants include alum, dextran, sulfate, large polymeric anions, oil& water emulsions, e.g. Freund's adjuvant, Freund's complete adjuvant, and the like. The GST-3 may also be conjugated to synthetic carrier proteins or synthetic antigens. A variety of hosts may be immunized to produce the polyclonal antibodies. Such hosts include rabbits, guinea pigs, rodents, e.g. mice, rats, sheep, goats, and the like. The GST-3 is administered to the host, usually intradermally, with an initial dosage followed by one or more, usually at least two, additional booster dosages. Following immunization, the blood from the host will be collected, followed by separation of the serum from the blood cells. The Ig present in the resultant antiserum may be further fractionated using known methods, such as ammonium salt fractionation, DEAE chromatography, and the like.

Monoclonal antibodies are produced by conventional techniques. Generally, the spleen and/or lymph nodes of an immunized host animal provide a source of plasma cells. The plasma cells are immortalized by fusion with myeloma cells to produce hybridoma cells. Culture supernatant from individual hybridomas is screened using standard techniques to identify those producing antibodies with the desired specificity. Suitable animals for production of monoclonal antibodies to the human protein include mouse, rat, hamster, etc. To raise antibodies against the mouse protein, the animal will generally be a hamster, guinea pig, rabbit, etc. The antibody may be purified from the hybridoma cell supernatants or ascites fluid by conventional techniques, e.g. affinity chromatography using GST-3 bound to an insoluble support, protein A sepharose, etc.

The antibody may be produced as a single chain, instead of the normal multimeric structure. Single chain antibodies are described in Jost et al. (1994) *J.B.C.* 269:26267–73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

For in vivo use, particularly for injection into humans, it is desirable to decrease the antigenicity of the antibody. An immune response of a recipient against the blocking agent will potentially decrease the period of time that the therapy is effective. Methods of humanizing antibodies are known in the art. The humanized antibody may be the product of an animal having transgenic human immunoglobulin constant region genes (see for example International Patent Applications WO 90/10077 and WO 90/04036). Alternatively, the antibody of interest may be engineered by recombinant DNA techniques to substitute the CH1, CH2, CH3, hinge domains, and/or the framework domain with the corresponding human sequence (see WO 92/02190).

The use of Ig cDNA for construction of chimeric immunoglobulin genes is known in the art (Liu et al. (1987) *P.N.A.S.* 84:3439 and (1987) *J. Immunol.* 139:3521). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) *Sequences of Proteins of Immunological Interest*, N.I.H. publication no. 91–3242. Human C region genes are readily available from known clones. The choice of isotype will be guided by the desired effector functions, such as complement fixation, or activity in antibody-dependent cellular cytotoxicity. Preferred isotypes are IgG1, IgG3 and IgG4. Either of the human light chain constant regions, kappa or lambda, may be used. The chimeric, humanized antibody is then expressed by conventional methods.

Antibody fragments, such as Fv, F(ab')$_2$ and Fab may be prepared by cleavage of the intact protein, e.g. by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

Consensus sequences of H and L J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g. SV-40 early promoter, (Okayama et al. (1983) *Mol. Cell. Bio.* 3:280), Rous sarcoma virus LTR (Gorman et al. (1982) *P.N.A.S.* 79:6777), and moloney murine leukemia virus LTR (Grosschedl et al. (1985) *Cell* 41:885); native Ig promoters, etc.

In yet other embodiments of the invention, the active agent is an agent that modulates, and generally decreases or down regulates, the expression of GST-3 in the host. Anti-sense molecules can be used to down-regulate expression of GST-3 in cells. The anti-sense reagent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al (1996), *Nature Biotechnol.* 14:840–844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993), supra, and Milligan et al., supra.) Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2–5'-O-pho 3'-NH-5'-O-phosphoroamidate. Peptide nucleic acids replace the entire ribose phosphodiester backbone with a peptide linkage. Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995), *Nucl. Acids Res.* 23:4434–42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. (1995), *Appl. Biochem. Biotechnol.* 54:43–56.

As mentioned above, an effective amount of the active agent is administered to the host, where "effective amount" means a dosage sufficient to produce a desired result. Generally, the desired result is at least a reduction in the amount of selectin binding as compared to a control.

In the subject methods, the active agent(s) may be administered to the host using any convenient means capable of resulting in the desired inhibition of selectin binding. Thus, the agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

As such, administration of the agents can be achieved in various ways, including oral, buccal, rectal, parenteral, intraperitoneal, intradermal, transdermal, intracheal, etc., administration.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Where the agent is a polypeptide, polynucleotide, analog or mimetic thereof, e.g. antisense composition, it may be introduced into tissues or host cells by any number of routes, including viral infection, microinjection, or fusion of vesicles. Jet injection may also be used for intramuscular administration, as described by Furth et al. (1992), *Anal Biochem* 205:365–368. The DNA may be coated onto gold microparticles, and delivered intradermally by a particle bombardment device, or "gene gun" as described in the literature (see, for example, Tang et al. (1992), *Nature* 356:152–154), where gold microprojectiles are coated with the GST-3 DNA, then bombarded into skin cells.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

The subject methods find use in the treatment of a variety of different disease conditions involving selectin binding interactions, particularly L-, E- or P- selectin, and more particularly L-selectin mediated binding events. Such disease conditions include those disease conditions associated with or resulting from the homing of leukocytes to sites of inflammation, the normal homing of lymphocytes to secondary lymph organs; and the like. Accordingly, specific disease conditions that may be treated with the subject methods include: acute or chronic inflammation; autoimmune and related disorders, e.g. systemic lupus erythematosus, rheumatoid arthritis, polyarteritis nodosa, polymyositis and dermatomyositis, progressive systemic sclerosis (diffuse scleroderma), glomerulonephritis, myasthenia gravis, Sjogren's syndrome, Hashimoto's disease and Graves' disease, adrenalitis, hypoparathyroidism, and associated diseases; pernicious anemia; diabetes; multiple sclerosis and related demyelinating diseases; uveitis pemphigus and pemphigoid; cirrhosis and other diseases of the liver; ulcerative colitis; myocarditis; regional enteritis; adult respiratory distress syndrome; local manifestations of drug reactions (dermatitis, etc.); inflammation-associated or allergic reaction patterns of the skin; atopic dermatitis and infantile eczema; contact dermatitis, psoriasis lichen planus; allergic enteropathies; atopic diseases, e.g. allergic rhinitis and bronchial asthma; transplant rejection (heart, kidney, lung, liver, pancreatic islet cell, others); hypersensitivity or destructive responses to infectious agents; poststreptococcal diseases e.g. cardiac manifestations of rheumatic fever, etc.; tissue rejection during transplantation; and the like.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as inflammation and pain associated therewith. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Kits with unit doses of the active agent, usually in oral or injectable doses, are provided. In such kits, in addition to the containers containing the unit doses will be an informational package insert describing the use and attendant benefits of the drugs in treating pathological condition of interest. Preferred compounds and unit doses are those described herein above.

The following examples are offered primarily for purposes of illustration. It will be readily apparent to those skilled in the art that the formulations, dosages, methods of administration, and other parameters of this invention may be further modified or substituted in various ways without departing from the spirit and scope of the invention.

EXPERIMENTAL

I. Identification of GST-1 & GST-2

Human ESTs that are related to the C6ST/KSST at the protein level were searched by using TBLASTN which compares a protein query sequence against a nucleotide sequence database translated in all 6 reading frames. (Karlin, Samuel and Stephen F. Altschul (1990). Methods for assessing the statistical significance of molecular sequence features by using general scoring schemes. Proc. Natl. Acad. Sci. USA 87:2264–68; Karlin, Samuel and Stephen F. Altschul (1993). Applications and statistics for multiple high-scoring segments in molecular sequences. Proc. Natl. Acad. Sci. USA 90:5873–7). As shown in Table 1, several ESTs, ranging from 228 to 861 bases, resulted in high scores. When compared over their entire length with the C6ST/KSST, the predicted amino acid identities ranged from 27% to 57%.

TABLE 1

Human ESTs related to the chick chondroitin 6/keratan sulfate sulfotransferase

| No. | mRNA source | Covering AA of C6ST/KSST | Identity of AA Sequences (%) | Contig Assignment |
| --- | --- | --- | --- | --- |
| 1 | infant brain | 347–451 | 42 | 1 |
| 2 | infant brain | 140–216 | 57 | 1 |
| 3 | adult heart | 405–451 | 42 | 1 |
| 4 | fetal lung | 89–375 | 30 | 2 |
| 5 | fetal liver/spleen | 332–403 | 27 | 2 |
| 6 | teratocarcinoma | 100–165 | 31 | 2 |

The cDNA clones corresponding to each EST were obtained from the ATCC and Research Genetics, Inc.,(Huntsville, Ala.) and sequenced in full to obtain further 3' information. Sequence alignment analysis revealed the presence of two distinct sequences ("contigs"), covering 74% (contig 1, starting at amino acid 137) and 78% (contig 2, starting at amino acid 100). Contig sequences 1 and 2 are apparently both complete at the 3' end, since both contain poly A tracts at the end of their 3' untranslated regions (UTR).

Expression of transcripts corresponding to the two contigs was examined in a number of human tissues by Northern analysis. Blots of poly $A^+$RNA (Clontech, Palo Alto, Calif.) were probed at high stringency with probes derived from the EST clones. A 3.1 kb band corresponding to contig 1 was detected in multiple human organs (heart, placenta, lung, liver, skeletal muscle, kidney, pancreas, spleen, lymph nodes, thymus) but most strongly in brain. Contig 2 was also broadly expressed in various organs (3.3 kb band), including lymph node and brain.

Full-length cDNAs containing the two contigs and predicting CS6T/KSST homologs were obtained by screening a human fetal brain λZAP cDNA library (Stratagene, La Jolla, Calif.) with labeled 700–800 bp restriction fragments (from EST 2 for contig 1 and from EST 5 for contig 2). Briefly, $10^6$ plaque-forming units were used to infect E. coli, which were then distributed on 20 plates. Duplicate filter lifts were performed. The probes were labeled with $^{32}P$ by random priming (Amersham), and hybridization was performed at 60° C. with high stringency washing. In both screens, multiple positive spots were obtained in the first round. Single positive clones were obtained after either the second or third round of screening. Multiple clones were sequenced for each gene and the presence of the ESTs was confirmed. As will be described below, the cDNAs contain open reading frames that encode predicted proteins of high homology to CS6T/KSST. The proteins encoded by these cDNAs were designated as GST 1 and GST 2, where "GST" denotes "glycosylsulfotransferase." GST 1 has been independently cloned by Fukuta et al., J. Biol. Chem. (1997) 272: 32321–8.

II. Identification of GST-3

ESTs potentially coding for novel human glycosyl sulfotransferases other than GST-1 & 2 were identified through a secondary homology screen, in which the peptide sequences of GST-1 and GST-2 were used as template in two parallel TBLASTN searches against a public (dbest) and a private genomic database (Lifeseq, Incyte Pharmaceuticals, Palo Alto, Calif.). Only matches that produced alignments with smallest sum probabilities P(N)<10⁻⁵ were selected from the output of the search, imported into a contig assembler (Sequencher 3.0, Gene Codes Corporation, Ann Arbor, Mich.) and assembled using the default settings of the program. The vast majority of these matches assembled into two contigs defined by GST-1 and GST-2. However, four particular ESTs found only in the private Lifeseq database did not assemble into either contig or with each other. These were termed GST-3 through GST-6.

III. GST-3 is Expressed in High Endothelial Venules

In order to investigate if any of the above putative human glycosyl sulfotransferases or similar genes were expressed in high endothelial venules, an HEV-derived cDNA pool for use as template in homology polymerase chain reaction (PCR) was prepared. In order to clone HEV genes, an expression library from the aforementioned HEV-derived cDNA was also generated. Briefly, total RNA (45 µg) was isolated from 10⁷ HEC. Since the amount of poly A⁺RNA was too limited for preparation of a cDNA library by conventional procedures, the Capfinder (SMART™) cDNA technology (CLONTECH) was used. In this technique, the reverse transcription reaction is primed by a modified oligo (dT) primer (containing a Not I site) and a "SMART" oligonucleotide which anneals to an oligo dC stretch added by reverse transcriptase (RT) at the 3' end of the first strand cDNA. The annealed oligonucleotide serves as a "switch" template for RT, resulting in the generation of single stranded cDNAs which are enriched for full length sequences and contain universal primer sites for subsequent long distance PCR amplification. This technology therefore makes it possible to generate high quality double stranded cDNA (from limiting amounts of RNA), which is sufficient to construct a library. According to the published test results for this technology, Capfinder cDNA is comparable to conventionally prepared cDNA in gene representation and is significantly enriched for full length cDNAs. The HEC cDNA generated by the Capfinder technology was evaluated by PCR for the presence of the following genes, which are known or suspected to be expressed in HEC: CD34 (Baumhueter et al., Science (1993) 262: 436–438), hevin (Girard & Springer, Immunity (1995) 2:113–123), fucosyltransferase VII (Maly et al., Cell (1996) 86: 643–653); β-1,6-N-acetylgl (C2GnT) (Bierhuizen & Fukuda., Proc. Natl. Acad. Sci. USA (1992) 89: 9326–9330), and fractalkine (Schall, Immunology Today (1997) 18:147). By this analysis, all of these cDNAs were detected in the HEC cDNA, and at least two of them (CD34 and C2GnT) were full length. With this validation of the HEC cDNA, a library was generated as follows: the double-stranded cDNA was ligated to Eco RI adapters, digested with Not I and cloned into the Not I and Eco RI sites of pCDNA1.1 (Invitrogen, Inc, Carlsbad, Calif.), which is a modified version of the eucaryotic expression vector pCDM8 (Aruffo et al., Proc. Natl. Acad. Sci. USA (1987) 84: 8753–8577). The resulting libary has a complexity of 500,000 independent clones and an average insert size of 1.1 kb, according to the characterization performed by CLONTECH.

HEV-derived Capfinder cDNA was used as a template for homology PCR with degenerate primers. In-frame translations of GST-1 and GST-2 were aligned with other known sulfotransferase protein sequences retrieved from the public databases. See FIG. 3. Three putative consensus regions were identified, and the following degenerate primers were synthesized to encode within these consensus regions a maximal number of possible permutations at the amino-acid level in order to cover a maximal number of novel sulfotransferases that may fall into these patterns.

These primers were (I=inosine):

```
                                          (SEQ ID NO:03)
A+:  5' TWYTWYCTITWYGARCCICTITGGCAYST      3'

(SEQ ID NO:04)
B+:  5' CTIAAICTISTICWRCTISTIMGIRAYCC      3'

(SEQ ID NO:05)
B-:  5' GGRTYICKIASIAGYWGIASIAGITTIAG      3'

(SEQ ID NO:06)
C-:  5' AGRTCYTCRTAICKIAGIAGIAKRTA         3'
```

In the first round PCR each reaction contained in a total volume of 50 µl 100 mM Tris-Cl (pH 8.3), 0.5 M KCl, 15 mM MgCl₂, forward and reverse primer (0.5 µM each), dATP, dCTP, dGTP, and dTTP (100 µM each), 0.25 units *Thermus aquaticus* DNA polymerase (Boehringer Mannheim #1647679), and 0.5 µl of HEV-message derived Cap-finder cDNA preparation (generated by Clontech Inc., cf. above). In "no template" control samples the cDNA was omitted.

Each reaction was cycled as follows: hold 4 min @ 94° C., then 35 cycles of [30 sec @ 94° C. followed by 30 sec @ 40° C. followed by 1 min @ 72° C.], then hold 6 min @72° C. Following completion of PCR a 20 µl aliqout of each reaction was analysed by standard horizontal agarose (1%) gel electrophoresis. No discernable band pattern was observed (data not shown).

Therefore the unfractionated products of the first round PCR were used as template in a second round PCR. Here each reaction contained in a total volume of 50 µl 100 mM Tris-Cl (pH 8.3), 0.5 M KCl, 15 mM MgCl₂, forward and reverse primer (0.5 µM each), dATP, dCTP, dGTP, and dTTP (100 µM each), 0.25 units *Thermus aquaticus* DNA polymerase (Boehringer Mannheim #1647679), and 1 µl of total PCR reaction from round 1 (cf. above). Each reaction was cycled as follows: hold 4 min @ 94° C., then 35 cycles of [30 sec @ 94° followed by 30 sec @ 45° C. followed by 1 min @ 72° C.], then hold 6 min @ 72The entire reactions were then fractionated by standard horizontal agarose (1%) gel electrophoresis. Bands appearing at positions 2.1, 2.2 and 2.3, see FIG. 4, were excised and DNA eluted from the gel using the QIAquick PCR purification kit (Qiagen Inc. #28104). Eluted DNA was then subcloned into the TA cloning vector pCR-II (stratagene) and *E-coli* transformed with recombinant plasmids. For each band eight colonies were expanded, and plasmid DNAs isolated and sequenced using standard dideoxynucleotide chain termination methodology with fluorimetric detection.

In order to map the amplicons generated by the above homology PCR, public (dbest) and private (Incyte Inc.) EST databases were screened with by the TBLASTX algorithm (Karlin & Altschul, 1990 & 1993; cf. above) using the sequences of these amplicons as query sequences. Four sequences amplified from from HEV-cDNA with primers B+ and C– aligned with >95% overall identity to Incyte EST #2620445 defined perviously as GST-3 (cf. above). All other query sequences did not pick up statistically significant matches in the specified databases.

IV. GST-3 is Expressed in HEC

From the extended DNA sequence of Lifeseq clone #2620445=GST-3 we designed a nondegenerate primer pair located within the incomplete open reading frame encoded by this EST.

Forward: 5'AAACTCAAGAAGGAGGACCAACCCTACTATGTGATGC 3'  (SEQ ID NO: 07)

Reverse: 5'ATAAAGCTTGTGGATTTGTTCAGGGACATTCCAGGTAGACAGAAGAT 3' (SEQ NO: 08)

Using RT-PCR, a PCR product of appropriate length (500 bp) was amplified from HEC cDNA with this primer pair. This product could not be amplified from cDNAs prepared from tonsillar lymphocytes or primary cultured human umbilical vein endothelial cells (HUVEC). See FIG. 5 Control primers for hypoxanthine phosphoribosyl transferase (HPRT, a ubiquitously expressed cellular "housekeeping enzyme") were used in parallel to establish that similar amounts of template were used in each set of PCR reactions and that none of the template DNAs were substantially degraded. These RT-PCR results confirm that the gene corresponding to the PCR product is expressed in HEC but not in lymphocytes or HUVEC. Northern analysis has failed to detect mRNA for the new gene in a variety of human tissues and organs, establishing that the expression of this gene is is highly restricted.

V. GST-3 Cloning

A full length cDNA from the HEC library described in the previous section was cloned as follows. The pool selection procedure described in Bakker et al., J. Biol. Chem. (1997) 272:29942–6) was used to quickly isolate the cDNA. It was first established that the relevant template was contained within the library by successfully amplifying the above described PCR product from the library stock comprising the entire library. An aliquot of this bacterial stock was then divided into 200 pools of 2000–3000 colonies each. Each pool was plated out on LB plates and the colonies were allowed to grow to a healthy size. The colonies were harvested in LB and allowed to grow further at 37° C., at which time glycerol stocks were prepared from each pool. By PCR analysis of the pools, nine positives were identified in this first round of screening. The corresponding bacterial stock for one of these pools was then titered and plated at 100 colony forming units (cfu) per plate in 40 plates. Plates were grown, harvested, preserved and analyzed as in the first round, resulting in the identification of three positive subpools. At this stage, one of the three positive pools was plated at a density (300 cfu) so that individual colonies could be analyzed by PCR. One cDNA clone was obtained by this approach. It contains a complete open reading frame which which encodes a novel 386 amino acid protein, termed GST-3. This full length cDNA sequence was now used as template in a BLASTN search of the public (dbest) and Lifeseq EST databases. In this manner, two so far unrecognized ESTs #2617407 (from Lifeseq; derived from a human gall bladder cDNA library) and g2262929 (from the mouse EST collection included in the dbest database, derived from a murine mammary gland cDNA library) were identified. The former EST included the 5' end of GST-3 open reading frame. Since this EST was generated with an oligo dT-primer, it contains therefore the entire open reading frame plus all 3' untranslated sequence of the human GST-3 cDNA. This EST was retrieved from Incyte in the form of a plasmid-transformed E. coli culture, expanded into Luria Bertoni Medium (with 0.1 mg/ml Ampicillin), plasmid isolated from a 500 ml culture, and sequenced using standard dideoxynucleotide chain termination methodology with fluorimetric detection. Since, in contrast to the Cap-finder methodology employed in generation of our HEV-library, no PCR-step was used in generating the full length GST-3 Lifeseq EST Incyte #2167407, the GST-3 sequence obtained from Incyte #2617407 is free of PCR errors. The sequence is provided in SEQ ID NO:01 and shown in FIG. 1.

VI. Characterization of GST-3

Three cDNA clones which encode three different human homologs for C6ST/KSST have been obtained. The predicted GST proteins are type 2 membrane proteins 411, 477, and 386 amino acids in length, respectively. Each has a relatively short transmembrane domain and a short amino-terminal cytoplasmic tail. Table 2 demonstrates the high homologies among the 3 human proteins and the chick CS6T/KSST. Overall homologies at the amino acid level ranged from 28% to 40% identity. Strikingly, there are three regions of 16 to 29 amino acids in which identity among the three GSTs ranged from 50–59% and similarity ranged from 65–94%. See FIG. 6. In FIG. 6 shows that all four of the sulfotransferases are type II transmembrane proteins with short cytoplasmic tails (™). There are three regions (region A, B and C) in which identities among the human GSTs range from 50–59% and similarities range from 65 to 94%. The amino acid sequence for the regions are:

A: (T/S)XRSGSSF(V/F)G(Q/E)LFXQX(P/L)(D/E)VF(F/Y)L(F/Y/M)EP(L/V/A)(W/Y)HV SEQ ID NO:10
B: L(N/D)L(K/H)(V/I)(I/V)XLVRDPR(A/G)(V/I)(LAF) SEQ ID NO:11
C: PXXL(Q/K)XXY(L/M)(L/V)VRYEDL(A/V)XXP (SEQ ID NO:12)

TABLE 2

Percent amino acid identities for the predicted coding sequences

|  | GST 1 | GST 2 | GST 3 | CS6T/KSST |
|---|---|---|---|---|
| GST 1 | — | 31 | 32 | 40 |
| GST 2 | — | — | 35 | 28 |
| GST 3 | — | — | — | 31 |

VII. GST-3 Sulfates GLYCAM-1

Figure 7:
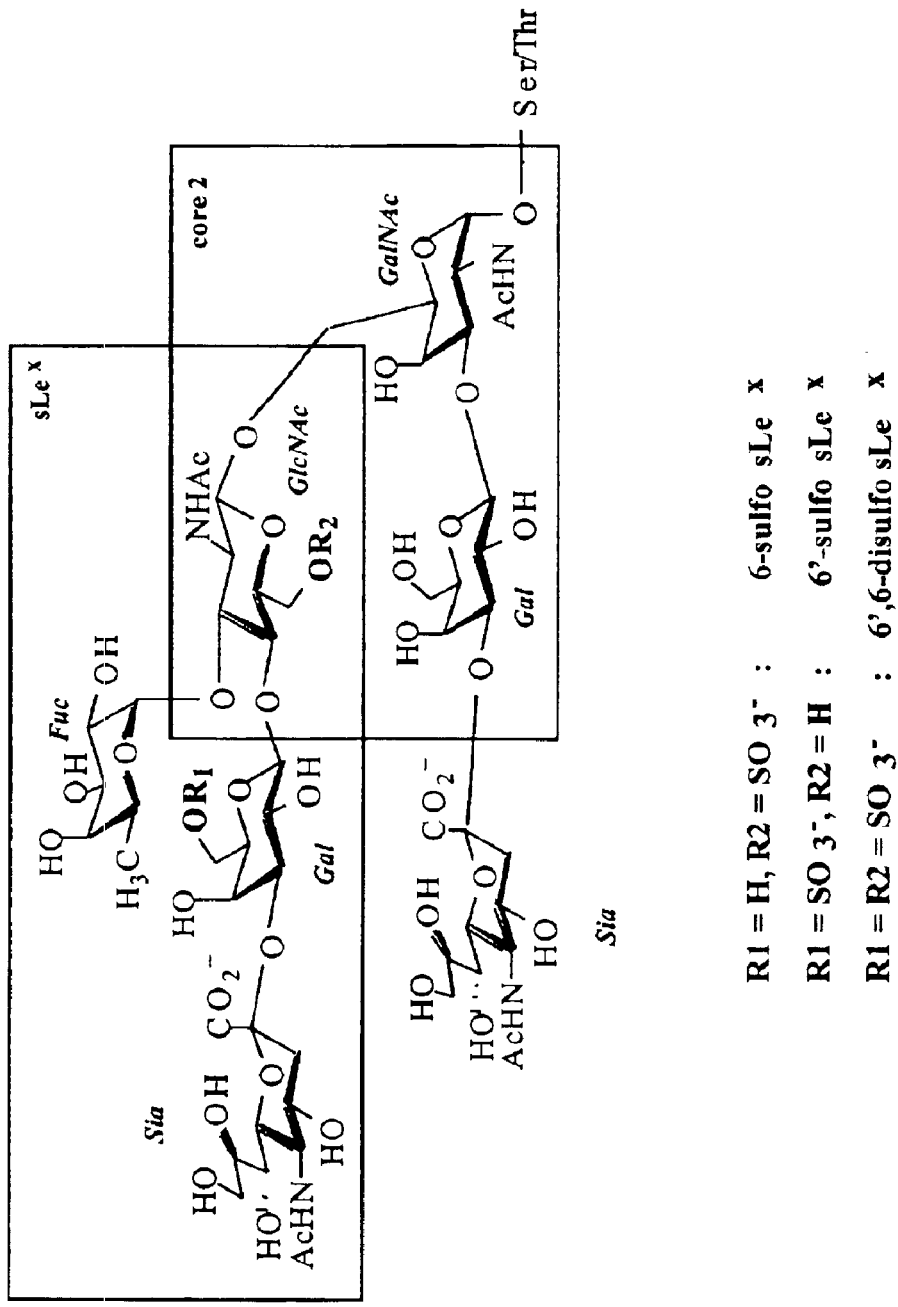
FIG. 7 provides a graphical representation of the amount of sulfate (SO$_4$) incorporation into GlyCAM-1 in COS7 cells cotransfected with: (a) GlyCAM-1/Ig expression plasmid plus GST-3 expression plasmid; and (b) GlyCAM-1/Ig expression plasmid plus vector lacking GST-3 insert; and (c) untransfected cells.

In expression experiments, the sulfotransferase activity of the GST 3 protein by transient expression of its cDNA into COS cells has been investigated. Since the HEC library yielding the GST 3 cDNA was in the pcDNA1.1 expression vector, there was no need subclone the GST 3 insert prior to transfection. Co-transfection of the GST 3 cDNA with a cDNA encoding a GlyCAM-1/human IgGl Fc chimera resulted in a >10 fold enhanced incorporation of $^{35}$S-SO$_4$ relative to transfection with the GlyCAM-1 chimera alone. Co-transfection with vector cDNA had no effect. By SDS-PAGE analysis, incorporation of $^{35}$S-SO$_4$ counts into the GlyCAM-1 chimera was confirmed. The results are shown in FIG. 7. The results indicate that GST 3 encodes a sulfotransferase that can utilize GlyCAM-1 as an acceptor.

It is apparent from the above results and discussion that a novel human glycosyl sulfotransferase, as well as polypeptides related thereto and nucleic acid compositions encoding the same are provided by the subject invention. These polypeptide and nucleic acid compositions find use in a variety of diverse applications, including research, diagnostic, screening and therapeutic applications. Also provided are improved methods of treating diseases associated with selectin-sulfated ligand mediated binding events, since agents that selectively reduce or inhibit the activity of the subject enzyme are employed, so that other sulfotransferases whose activity is beneficial are not adversely affected.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. An isolated nucleic acid molecule that hybridizes under stringent conditions to a nucleic acid molecule comprising the nucleotide sequence set forth in SEQ ID NO:01, or its complementary sequence, wherein stringent hybridization conditions comprise hybridization at 50° C. or higher in a solution comprising 15 mM sodium chloride and 1.5 mM sodium citrate, wherein said nucleotide sequence encodes a polypeptide that catalyzes the transfer of a sulfate group from a sulfate donor to a sulfate acceptor.

2. An expression vector comprising the nucleic acid of claim 1.

3. An isolated host cell comprising the expression vector of claim 2.

4. The host cell of claim 3, wherein the cell is prokaryotic.

5. The host cell of claim 3, wherein the cell is eukaryotic.

6. A method of producing a glycosyl sulfotransferase-3 polypeptide, said method comprising:

growing a cell according to claim 3, whereby said polypeptide is expressed; and isolating said polypeptide.

7. The isolated nucleic acid of claim 1, wherein said nucleic acid comprises the nucleotide sequence set forth in SEQ ID NO:1.

8. A composition comprising the nucleic acid of claim 1.

9. The composition according to claim 8, wherein said composition further comprises a test agent.

10. The composition according to claim 8, wherein said composition further comprises a sulfate donor.

11. The composition according to claim 8, wherein said composition further comprises a sulfate acceptor.

12. The composition according to claim 11, wherein said sulfate acceptor is a selectin.

13. The expression vector of claim 2, wherein said nucleic acid is operably linked to an exogenous control region.

* * * * *

UNITED STATES PATENT AND TRADEMARK OFFICE
CERTIFICATE OF CORRECTION

| | |
|---|---|
| PATENT NO. | : 6,967,093 B2 |
| DATED | : November 22, 2005 |
| INVENTOR(S) | : Bistrup, Annette et al. |

Page 1 of 1

It is certified that error appears in the above-identified patent and that said Letters Patent is hereby corrected as shown below:

<u>Column 1,</u>
Lines 8-9, before "Field of Invention" should be -- This invention was made with Government support under Grant No. GM23547, awarded by the National Institutes of Health. The Government has certain rights in this invention. --.

Signed and Sealed this

Thirtieth Day of May, 2006

JON W. DUDAS
*Director of the United States Patent and Trademark Office*

SEQUENCE LISTING

<160> NUMBER OF SEQ ID NOS: 9

<210> SEQ ID NO 1
<211> LENGTH: 2032
<212> TYPE: DNA
<213> ORGANISM: Homo sapiens

<400> SEQUENCE: 1

```
ggctcgaggc caggatgcct ccagtctggg ggaaaatgct tcctcatttg cttctcccag      60
cccacctcaa gcagtctccc caccccttga gtctcagcag tgttaaagct gttactttca     120
cagcttcctg ggagcgagtg ctttctcaag cccgtcttgc aaggtcttcc acttcagcac     180
aatgctactg cctaaaaaaa tgaagctcct gctgtttctg gtttcccaga tggccatctt     240
ggctctattc ttccacatgt acagccacaa catcagctcc ctgtctatga aggcacagcc     300
cgagcgcatg cacgtgctgg ttctgtcttc ctggcgctct ggctcttctt ttgtggggca     360
gcttttgggg cagcacccag atgttttcta cctgatggag cccgcctggc acgtgtggat     420
gaccttcaag cagagcaccg cctggatgct gcacatggct gtgcgggatc tgatacgggc     480
cgtcttcttg tgcgacatga gcgtctttga tgcctacatg gaacctggtc cccggagaca     540
gtccagcctc tttcagtggg agaacagccg ggccctgtgt tctgcacctg cctgtgacat     600
catcccacaa gatgaaatca tcccccgggc tcactgcagg ctcctgtgca gtcaacagcc     660
ctttgaggtg gtggagaagg cctgccgctc ctacagccac gtggtgctca aggaggtgcg     720
cttcttcaac ctgcagtccc tctacccgct gctgaaagac ccctccctca acctgcatat     780
cgtgcacctg gtccgggacc cccgggccgt gttccgttcc cgagaacgca caaagggaga     840
tctcatgatt gacagtcgca ttgtgatggg gcagcatgag cagaaactca agaaggagga     900
ccaaccctac tatgtgatgc aggtcatctg ccaaagccag ctggagatct acaagaccat     960
ccagtccttg cccaaggccc tgcaggaacg ctacctgctt gtgcgctatg aggacctggc    1020
tcgagcccct gtggcccaga cttcccgaat gtatgaattc gtgggattgg aattcttgcc    1080
ccatcttcag acctgggtgc ataacatcac ccgaggcaag ggcatggtg accacgcttt     1140 ccacacaaat gccagggatg cccttaatgt ctcccaggct tggcgctggt ctttgcccta    1200
tgaaaaggtt tctcgacttc agaaagcctg tggcgatgcc atgaatttgc tgggctaccg    1260
ccacgtcaga tctgaacaag aacagagaaa cctgttgctg gatcttctgt ctacctggac    1320
tgtccctgag caaatccact aagagggttg agaaggcttt gctgccacct ggtgtcagcc    1380
tcagtcactt tctctgaatg cttctgagcc ttgcctacat ctctgagcct taactacatg    1440
tctgtgggta tcacactgag tgtgagttgt gtccacacgt gctcaagcag aaggactttt    1500
gtgtccatgc ttgtgtctag aaaacagact ggggaacctt atgtgagcag cacatcccac    1560
cagtgaaaca gggtattgct cttcttcttt tcttgatctt cctgtctggg cagacttcag    1620
agactttgtg gcctggaggc ctattaagca cgacacagta tcagtggaat tgatccataa    1680
```

-continued

```
acctccctgt ccacatcttg cccaatgggg aatggatctt tcaccaaaga gctcaccagc     1740
attttccaca gagatgcaaa ttctgagccc ttggagttcc cagtggattc aaggaaggaa     1800
gtgggaacaa ggttggatgc ctacttatga gcttgaccat cacagctatc ggtaatcaga     1860
aatatgaaac aaaatctctg cacaaaagag caagctctta agttcacagg gtgcctgggc     1920
tgcatttgaa tatcacttcc cctctgcatt ttcccatcac atagaagact ttgacctgtg     1980
aagctgccat ctgttaatac taaaattccc aataagaaa aaaaaaaaa aa              2032
```

<210> SEQ ID NO 2
<211> LENGTH: 386
<212> TYPE: PRT
<213> ORGANISM: Homo sapiens

<400> SEQUENCE: 2

```
Met Leu Leu Pro Lys Lys Met Lys Leu Leu Leu Phe Leu Val Ser Gln
  1               5                  10                  15

Met Ala Ile Leu Ala Leu Phe Phe His Met Tyr Ser His Asn Ile Ser
             20                  25                  30

Ser Leu Ser Met Lys Ala Gln Pro Glu Arg Met His Val Leu Val Leu
         35                  40                  45

Ser Ser Trp Arg Ser Gly Ser Ser Phe Val Gly Gln Leu Phe Gly Gln
     50                  55                  60

His Pro Asp Val Phe Tyr Leu Met Glu Pro Ala Trp His Val Trp Met
 65                  70                  75                  80

Thr Phe Lys Gln Ser Thr Ala Trp Met Leu His Met Ala Val Arg Asp
                 85                  90                  95

Leu Ile Arg Ala Val Phe Leu Cys Asp Met Ser Val Phe Asp Ala Tyr
            100                 105                 110

Met Glu Pro Gly Pro Arg Arg Gln Ser Ser Leu Phe Gln Trp Glu Asn
        115                 120                 125

Ser Arg Ala Leu Cys Ser Ala Pro Ala Cys Asp Ile Ile Pro Gln Asp
    130                 135                 140

Glu Ile Ile Pro Arg Ala His Cys Arg Leu Leu Cys Ser Gln Gln Pro
145                 150                 155                 160

Phe Glu Val Val Glu Lys Ala Cys Arg Ser Tyr Ser His Val Val Leu
                165                 170                 175

Lys Glu Val Arg Phe Phe Asn Leu Gln Ser Leu Tyr Pro Leu Leu Lys
            180                 185                 190

Asp Pro Ser Leu Asn Leu His Ile Val His Leu Val Arg Asp Pro Arg
        195                 200                 205

Ala Val Phe Arg Ser Arg Glu Arg Thr Lys Gly Asp Leu Met Ile Asp
    210                 215                 220

Ser Arg Ile Val Met Gly Gln His Glu Gln Lys Leu Lys Lys Glu Asp
225                 230                 235                 240

Gln Pro Tyr Tyr Val Met Gln Val Ile Cys Gln Ser Gln Leu Glu Ile
                245                 250                 255

Tyr Lys Thr Ile Gln Ser Leu Pro Lys Ala Leu Gln Glu Arg Tyr Leu
            260                 265                 270

Leu Val Arg Tyr Glu Asp Leu Ala Arg Ala Pro Val Ala Gln Thr Ser
        275                 280                 285

Arg Met Tyr Glu Phe Val Gly Leu Glu Phe Leu Pro His Leu Gln Thr
    290                 295                 300

Trp Val His Asn Ile Thr Arg Gly Lys Gly Met Gly Asp His Ala Phe
305                 310                 315                 320
```

His Thr Asn Ala Arg Asp Ala Leu Asn Val Ser Gln Ala Trp Arg Trp
                325                 330                 335

Ser Leu Pro Tyr Glu Lys Val Ser Arg Leu Gln Lys Ala Cys Gly Asp
            340                 345                 350

Ala Met Asn Leu Leu Gly Tyr Arg His Val Arg Ser Glu Gln Glu Gln
        355                 360                 365

Arg Asn Leu Leu Leu Asp Leu Leu Ser Thr Trp Thr Val Pro Glu Gln
    370                 375                 380

Ile His
385

<210> SEQ ID NO 3
<211> LENGTH: 29
<212> TYPE: DNA
<213> ORGANISM: Artificial Sequence
<220> FEATURE:
<223> OTHER INFORMATION: primer
<221> NAME/KEY: misc_feature
<222> LOCATION: (0)...(0)
<223> OTHER INFORMATION: n=inosine

<400> SEQUENCE: 3
twytwyctnt wygarccnct ntggcayst                                           29

<210> SEQ ID NO 4
<211> LENGTH: 29
<212> TYPE: DNA
<213> ORGANISM: Artificial Sequence
<220> FEATURE:
<223> OTHER INFORMATION: primer
<221> NAME/KEY: misc_feature
<222> LOCATION: (0)...(0)
<223> OTHER INFORMATION: n=inosine

<400> SEQUENCE: 4
ctnaanctns tncwrctnst nmgnraycc                                           29

<210> SEQ ID NO 5
<211> LENGTH: 29
<212> TYPE: DNA
<213> ORGANISM: Artificial Sequence
<220> FEATURE:
<223> OTHER INFORMATION: primer
<221> NAME/KEY: misc_feature
<222> LOCATION: (0)...(0)
<223> OTHER INFORMATION: n=inosine

<400> SEQUENCE: 5
ggrtynckna snagywgnas nagnttnag                                           29

<210> SEQ ID NO 6
<211> LENGTH: 26
<212> TYPE: DNA
<213> ORGANISM: Artificial Sequence
<220> FEATURE:
<223> OTHER INFORMATION: primer
<221> NAME/KEY: misc_feature
<222> LOCATION: (0)...(0)
<223> OTHER INFORMATION: n=inosine

<400> SEQUENCE: 6
agrtcytcrt ancknagnag nakrta                                              26

<210> SEQ ID NO 7
<211> LENGTH: 37

```
-continued

<212> TYPE: DNA
<213> ORGANISM: Homo sapiens

<400> SEQUENCE: 7
aaactcaaga aggaggacca accctactat gtgatgc                              37

<210> SEQ ID NO 8
<211> LENGTH: 47
<212> TYPE: DNA
<213> ORGANISM: Homo sapiens

<400> SEQUENCE: 8
ataaagcttg tggatttgtt cagggacatt ccaggtagac agaagat                   47

<210> SEQ ID NO 9
<211> LENGTH: 6
<212> TYPE: PRT
<213> ORGANISM: Homo sapiens

<400> SEQUENCE: 9

Val Arg Tyr Glu Asp Leu
1               5
```